United States Patent
Guillon et al.

(10) Patent No.: US 9,454,021 B2
(45) Date of Patent: Sep. 27, 2016

(54) CONTACT LENSES

(75) Inventors: Michel Lucien Guillon, St. Laurence (JE); Cecile Adrienne Maissa, London (GB)

(73) Assignee: OPTOMETRIC TECHNOLOGY GROUP LTD., London (GB)

( * ) Notice: Subject to any disclaimer, the term of this patent is extended or adjusted under 35 U.S.C. 154(b) by 295 days.

(21) Appl. No.: 13/980,279

(22) PCT Filed: Jan. 18, 2012

(86) PCT No.: PCT/GB2012/050109
§ 371 (c)(1),
(2), (4) Date: Feb. 6, 2014

(87) PCT Pub. No.: WO2012/098398
PCT Pub. Date: Jul. 26, 2012

(65) Prior Publication Data
US 2014/0152953 A1 Jun. 5, 2014

(30) Foreign Application Priority Data
Jan. 18, 2011 (GB) .................................. 1100820.8

(51) Int. Cl.
*G02C 1/00* (2006.01)
*G02C 7/08* (2006.01)
(Continued)

(52) U.S. Cl.
CPC ............... *G02C 7/083* (2013.01); *A61F 2/145* (2013.01); *A61F 2/16* (2013.01); *A61F 2/1635* (2013.01); *G02B 1/043* (2013.01); *G02C 7/04* (2013.01); *G02C 7/049* (2013.01); *G02C 7/081* (2013.01);
(Continued)

(58) Field of Classification Search
CPC ........ G02C 7/04; G02C 7/041; G02C 7/042; G02C 7/045; G02C 7/048; G02C 7/049; G02C 11/10
USPC ................. 351/158, 159.02, 159.03, 159.05, 351/159.1, 159.11
See application file for complete search history.

(56) References Cited

U.S. PATENT DOCUMENTS

| 4,188,373 A | 2/1980 | Krezanoski |
| 5,448,312 A | 9/1995 | Roffman et al. |

(Continued)

FOREIGN PATENT DOCUMENTS

| GB | 2410029 A | 7/2005 |
| JP | 2001-290101 A | 10/2001 |

(Continued)

OTHER PUBLICATIONS

Benjamin, et al. Presbyopia and Influence of Aging on Prescription of Contact Lenses. In Contact Lens Practice edited by Ruben M. & Guillon M. Chapman & Hall, London, UK.. 1994; Ch 33, 763-828.
(Continued)

*Primary Examiner* — Huy K Mai
(74) *Attorney, Agent, or Firm* — Wilson Sonsini Goodrich & Rosati P.C.

(57) ABSTRACT

The present invention provides a contact lens manufactured at least partially from an intelligent polymer, the lens having a relaxed state which, upon application of a first stimulus forms a first corrective shape and which, upon application of a second stimulus, forms a second corrective shape, wherein the corrective effect provided by the lens in the relaxed state is intermediate to the corrective visual effects provided by the first and second corrective shapes.

38 Claims, 13 Drawing Sheets

(51) Int. Cl.
*A61F 2/16* (2006.01)
*G02B 1/04* (2006.01)
*G02C 7/04* (2006.01)
*A61F 2/14* (2006.01)
*G02C 11/00* (2006.01)
*B82Y 20/00* (2011.01)

(52) U.S. Cl.
CPC ............... *G02C 7/085* (2013.01); *G02C 11/10* (2013.01); *B82Y 20/00* (2013.01); *Y10S 977/932* (2013.01)

(56) References Cited

U.S. PATENT DOCUMENTS

| | | | |
|---|---|---|---|
| 5,485,228 | A | 1/1996 | Roffman et al. |
| 5,503,893 | A | 4/1996 | Evans et al. |
| 5,835,192 | A | 11/1998 | Roffman et al. |
| 5,840,338 | A * | 11/1998 | Roos .................. A61K 8/042 424/484 |
| 6,179,420 | B1 | 1/2001 | Roffman et al. |
| 6,388,043 | B1 | 5/2002 | Langer et al. |
| 6,511,178 | B1 | 1/2003 | Roffman et al. |
| 7,575,807 | B1 | 8/2009 | Barvosa-Carter et al. |
| 8,167,427 | B2 * | 5/2012 | Guillon .................. G02B 3/10 351/159.02 |
| 2005/0021139 | A1 | 1/2005 | Shadduck |
| 2007/0100445 | A1 | 5/2007 | Shadduck |
| 2007/0196430 | A1 | 8/2007 | Shahinpoor et al. |
| 2008/0050423 | A1 * | 2/2008 | Hsiue .................. A61L 27/3633 424/443 |

FOREIGN PATENT DOCUMENTS

| | | |
|---|---|---|
| WO | WO 94/23334 A1 | 10/1994 |
| WO | WO 97/00275 | 1/1997 |
| WO | WO 01/02895 A1 | 1/2001 |
| WO | WO 01/35880 A1 | 5/2001 |
| WO | WO 2004/021924 A2 | 3/2004 |
| WO | WO 2004/072689 A2 | 8/2004 |
| WO | WO 2005/050291 A1 | 6/2005 |
| WO | WO 2005/096029 A1 | 10/2005 |
| WO | WO 2006/055707 A2 | 5/2006 |
| WO | WO 2005/059632 A1 | 6/2006 |
| WO | WO 2008/024766 A2 | 2/2008 |
| WO | WO 2009/108349 A1 | 9/2009 |
| WO | WO 2012/098398 A1 | 7/2012 |

OTHER PUBLICATIONS

Hu. Synthesis and application of modulated polymer gels. Science. Jul. 28, 1995;269(5223):525-7.
International preliminary report on patentability dated Jul. 23, 2013 for PCT/GB2012/050109.
International search report and written opinion dated Mar. 23, 2012 for PCT/GB2012/050109.
Karauchi, et al. Deformation behaviours of polymer gels in electric field. In Polymer Gels. Ed. D. DeRossi et al Plenum Press, NY, 1991, pp. 237.
Li, et al. Shape memory gels made by the modulated gel technology. J Appl Polym Sci. 1997; 63:1173-1178.
Tanaka, et al. Collapse of gels in an electric field. Science. Oct. 29, 1982;218(4571):467-9.
Tanaka, et al. Polymer gels that can recognize and recover molecules. Faraday Discuss. 1995; 101:201-206.

* cited by examiner

CONTACT LENSES

This application is a §371 U.S. National Stage of International Application No. PCT/GB2012/050109, filed on Jan. 18, 2012, which claims the benefit of GB Application No. 1100820.8, filed on Jan. 18, 2011, incorporated herein by reference.

BRIEF SUMMARY

The present invention relates to lenses such as contact lenses, intra-ocular lenses, implant lenses, inlay lenses, onlay lenses or any other ophthalmic refracture devices. For ease of reference these lenses will be referred to collectively as "contact lenses". Thus any reference to "contact lenses", "contact lens", "lenses", "lens" and the like will be understood to include at least the above-mentioned lenses.

Figure 1:
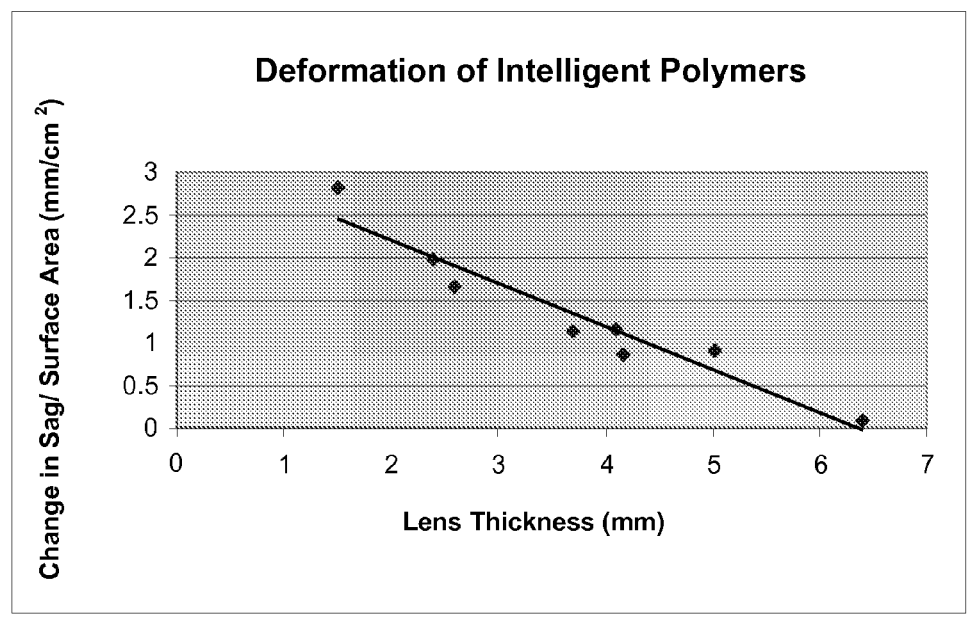
FIG. 1 shows changes in sag per surface area (mm/cm$^2$) in view of lens thickness.

As the popularity of contact lenses has increased over the use of glasses to correct vision, it has become desirable to address the problems encountered by users who require correction of their vision for both near and distance viewing. It is therefore desirable to develop bifocal (two foci), and preferably multi-focal (more than two foci including continuously changing focus and multiple discrete foci) contact lenses.

Examples of arrangements of bifocal contact lenses are known. One arrangement known as Alternating Image bifocals or Alternating Vision bifocals has a distance viewing region located in the upper portion of the lens and a near-viewing portion located in the bottom portion of the lens. The two parts of the lens are separated by a line extending across the lens that may be straight or curved. A review of typical designs for these lenses can be found in Ruben M. & Guillon M. (1994), Chapter 33 Presbyopia and Influence of Aging on Prescription of Contact Lenses (W J Benjamin, I M Borish) Chapman & Hall, London, UK.

These bifocal contact lenses function by taking a different position in straight ahead gaze and in down gaze. Theoretically, in straight ahead gaze the pupil is covered by the distance zone and in down gaze the contact lens is higher and the pupil is covered by the near zone. However, this arrangement suffers from certain disadvantages.

One disadvantage of this arrangement is that it is difficult to precisely control the movement of the lens so that the pupil is alternately covered by the near and distance position. To achieve this, a skilful process that is time-consuming and not always successful is required. Failure to achieve optimal pupil coverage has the disadvantage that the user looks through both the distance and near portions of the lens simultaneously resulting at times in two images at once being seen which is known as "ghosting" and habitually in a decrease in visual acuity compared with that achieved with spectacles.

A second disadvantage is that for an Alternating Vision bifocal to perform optically it is required to move significantly more than is optimum for comfort and thus the user may experience some discomfort. Further, it may be necessary to provide features on the lens to increase its movement during down gaze in order to position the near portion of the lens in front of the pupil. However, these features may increase the thickness and the irregularity of the contact lens which may result in lower comfort than the conventional simple design.

A still further disadvantage of this arrangement is that the separation line provides a discontinuity on the surface of the contact lens. If the line is situated on the anterior surface of the contact lens it can catch the eyelid, create discomfort, and pull the lens out of position at least temporarily impairing the user's vision. If the separation line is placed on the back surface of the lens it may create mechanical trauma to the ocular tissue.

An alternative lens arrangement is known under the generic term of Simultaneous Image bifocal or multifocal. These contact lenses are typically formed from two or more concentric zones of alternating distance and near power or a single zone of continuously changing power (progressive). Two options are available. In the first a centre near contact lens is known in which the near power is at the centre of the lens. In the second, a centre distance contact lens with the opposite arrangement is known. Typically for the progressive design the near portion will be in the centre but the opposite arrangement is known. Concentric zones designs are commonly available both in centre near or centre distance designs. (Ruben M. & Guillon M. (1994), Chapter 33 Presbyopia and Influence of Aging on Prescription of Contact Lenses (W J Benjamin, I M Borish) Chapman & Hall, London, UK.).

One benefit of these lenses compared to Alternating Vision bifocal lenses is that they do not require movement to perform as bifocals. However, they do require excellent centration during both distance and near gaze. This requirement is a disadvantage compared to single vision contact lenses in making fitting more exacting.

The principal disadvantage of the Simultaneous Image bifocal or multifocal lenses is that in order to function, they focus at least a distance and near image on the retina at all times. The associated disadvantage is that they produce a retinal image of poorer quality than that obtained with single vision contact lenses or spectacles. For example, during distance gaze, only part of the pupil is covered by the distance optics which form the in focus image; the rest of the pupil is covered by out of focus intermediate and/or near zones which degrade the quality of the image produced on the retina and consequently decrease visual performance, producing visual complaints. This problem is especially pronounced under poor light such as when the user is indoor at night or driving at night. The opposite situation is present during near gaze, when parts of the pupil are covered by out of focus intermediate and/or distance zones, decreasing the quality of the near signal.

A still further disadvantage is that the size of pupils varies between patients and more importantly for each patient with different levels of luminance. This has the drawback that the exact percentage of light forming the distance, near or any intermediate image is not controlled. Various suggestions have been made to address this through the use of "pupil intelligent" arrangements and/or the use of "binocular pair" where one contact lens favours near and one favours distance vision. For example, one lens may have a centre near design and the other a centre distance design. However, even with these modifications, the above-mentioned drawbacks remain. In particular, the intensity of the focussed light which generates a proportional retinal signal is attenuated leading to a loss of contrast between objects, reducing their visibility.

In a further alternative arrangement it has been proposed to use two materials of different refractive indexes to produce either Alternating Vision or Simultaneous Vision bifocal or multifocal lenses. However these differing manufacturing processes do not overcome the mechanical problems of the former and the visual problems of the latter.

In other alternative arrangements Simultaneous Vision bifocal lenses are produced utilising diffractive rather than refractive principles. The disadvantages of the compromised vision are similar in both cases and in addition a significant amount of light is lost making vision at night even more problematic than with refractive contact lenses.

Examples of prior art contact lenses are provided in U.S. Pat. No. 6,511,178, U.S. Pat. No. 5,835,192, U.S. Pat. No. 6,179,420, U.S. Pat. No. 5,485,228 and U.S. Pat. No. 5,448,312.

In a more recently developed alternative arrangement, contact lenses have been at least partially manufactured from so-called intelligent polymers which change shape.

Intelligent polymers are materials which have the capacity to respond to external stimuli such as temperature, pH, ionic strength, light, electric field, magnetic field, shear forces or a chemical trigger. The responsive polymers are generally polymer networks. These networks are polymer-polymer compositions where there are favourable interactions between the constituent polymers. The interaction may be covalent bonding, coulombic attraction, hydrogen bonding, Van der Waals attractions, and physical interactions such as entanglement.

Examples of responsive polymers can be found in U.S. Pat. No. 5,503,893, WO 97/00275, U.S. Pat. No. 4,188,373, U.S. Pat. No. 5,252,318, WO 95/24430, Katoaka K et al. Journal of the American Chemical Society. December 1998, Tanaka T et al Faraday Discuss, 101, 201 (1995), Li Y, Hu Z, Chen Y. "Shape memory gels made by the modulated gel technology, J Appl Poly Sci 63: 1173-1178 (1997), Hu Z. Science 269:525 (1995), Tanaka et al Collapse of gels in an electric field Science 218:457-469 (1982), Osada Y, Ross-Murphy SB. Intelligent gels Scientific American, May 1993 pp 42 and Karauchi T et al "Deformation behaviours of polymer gels in electric field" In Polymer Gels. Ed. D. DeRossi et al Plenum Press, N Y, 1991, pp 237 which are incorporated herein by reference.

Examples of contact lenses which include intelligent polymers are provided in GB2410029, which is incorporated by reference. While these lenses overcome many of the problems associated with use of more conventional lenses discussed above, it has recently been discovered that, depending on the intelligent polymer used, the degree of correction that the lens is required to provide and also the type of lens, there may be a need for an improvement in certain circumstances.

More specifically, under certain conditions, it has been found that a number of intelligent polymers, following repeated stimulation exhibit fatigue and gradually begin to fail to return to their original shape. For the avoidance of doubt, as used herein in connection with intelligent polymers, the term 'fatigue' is not only used in its literal manner, but also encompasses any loss of activity or failure of the polymer to revert to its original shape which may arise as a result of conditions such as hysteresis or the presence of residual charge in regions of the intelligent polymer.

Additionally, for certain lens types, such as intraocular lenses, the use of thicker lenses with less curved surfaces is preferable. Such lenses require greater lens curve changes in percentage terms to function effectively. It has been found that there is a degree of proportionality between the magnitude of the stimulus necessary to change the shape of the intelligent polymer lens and the thickness of the lens. It has also been found that there is a degree of proportionality between the magnitude of the stimulus and the degree of the change of curvature, regardless of the thickness of the lens. Accordingly, where thick and relatively less curved lenses are required, the magnitude of the stimulus necessary to change the shape of the intelligent polymer may be high.

To demonstrate this, a prior art intraocular lens intelligent polymer lens arrangement was prepared from PVA/PAA. 100 mA was applied to samples of different thicknesses, ranging from 1 mm to 6 mm. The change in sag (mm per lens surface area, $cm^2$) was recorded and the results are provided as FIG. 1. As can be seen, a generally linear relationship between the change in sag and lens thickness was observed.

Extrapolation of the results to predict the degree of sag of a lens with a thickness between 0.250 mm and 0.050 mm, with an average typical value of 0.070 mm to 0.120 mm (which are typical thicknesses of corneal contact lenses) would give deformations of 3.18 mm and 3.16 mm respectively.

It is therefore desirable to provide bi-focal or multi-focal contact lenses which overcome the above-mentioned drawbacks and disadvantages.

Thus, according to a first aspect, there is provided a contact lens manufactured at least partially from an intelligent polymer, the lens having a relaxed state which, upon application of a first stimulus forms a first corrective shape and which, upon application of a second stimulus, forms a second corrective shape, wherein the corrective effect provided by the lens in the relaxed state is intermediate to the corrective visual effects provided by the first and second corrective shapes, and the lens reverts to its relaxed state following cessation of the first or second stimulus.

The contact lens of the present invention is capable of providing at least two degrees of visual correction. For example, the first or second stimulated shapes may provide a distance correction and the other of the first or second stimulated shapes may provide a near addition correction.

The shape of the lens when in the relaxed state preferably provides a degree of visual correction which is intermediate to the degrees of correction provided by the first or second stimulated shapes. The shape of the lens in the relaxed state may be any shape between the stimulated first and second shapes. The visual effect imparted by the shape of the contact lens when in the relaxed state may not necessarily provide any beneficial effect to the patient. For the avoidance of any doubt, where used herein, the term "intermediate" does not necessarily mean that the degree of correction when the lens is in the relaxed state is equidistant to the degrees of correction provided by the first and second stimulated shapes.

Refractive effect may be quantified using any technique known in the art. The use of dioptre units to quantify visual effect and degrees of correction are most preferred.

For example, in a patient requiring a distance correction of −4.00 D and a near addition correction of +2.00 D, the first and second stimulated shapes will provide these degrees of correction. The shape of the lens when in the relaxed state may provide an intermediate degree of correction of −3.00 D, which in itself may or may not improve the patient's vision.

In such arrangements, although the contact lens is capable of providing three degrees of correction, as only two are of benefit to the patient, the lens can be regarded as bifocal, rather than tri-focal.

In alternative arrangements, the degree of correction provided by the lens when in the relaxed state provides an optimised intermediate correction and thus can be considered as a trifocal lens.

Preferably, the degree of visual effect provided by the contact lens when in the relaxed state is equidistant from the degrees of visual correction provided by the first and second corrective shapes. However, this is not compulsory and in certain situations, it may be preferable for the degree of visual correction provided by the lens when in the relaxed state to be nearer to the degree of visual correction provided by the first shape than the second shape, or vice versa.

One main advantage of the contact lens of the present invention is that the magnitude of the stimulus exerted in either direction on the lens (e.g. increased curvature or decreased curvature) on the lens to achieve the visual correction provided by either the first or the second stimulated shape is lower than in earlier intelligent polymer contact lenses, which change shape between corrective extremes in only a single direction.

By reducing the magnitude of the stimuli exerted in any given direction on the intelligent polymer contact lens, the use of intelligent polymers which are more sensitive to fatigue (i.e. which are less likely to return to their original shape following repeated exposure to their trigger stimulus) will be possible. Further, for any intelligent gel, reducing the amplitude of the stimuli and thus the amplitude of deformation has the advantage of reducing gel fatigue and improving the response of the polymer throughout its desired life cycle.

In addition to reducing the magnitude of the stimuli, the magnitude of mechanical change when the shape of the lens is adjusted from the relaxed state to either of the first and/or second stimulated shapes is lower than in prior art intelligent lenses which change shape between corrective extremes. Clearly, in sensitive tissue, minimising the degree of mechanical movement of devices such as contact lenses is advantageous as the risk of disturbance of those tissues as well as unwanted movement of the lens is reduced or eliminated.

For certain contact lens types, for example, intraocular lenses, a thicker lens may be preferable. It has been discovered that the magnitude of the stimulus required to achieve the shape which provides the desired degree of correction is generally proportional to the thickness of the intelligent polymer lens. For example, for a given electric stimulus, decreasing the thickness by approximately a factor of 3 will increase the magnitude of the response by a factor of 2.5. However, providing the means to emit a stimulus of high magnitude within the confines of such lenses is challenging.

Further, the emission of strong stimuli in lenses increases the risk of discomfort or disturbance of the tissues adjacent to the lens. Thus, in known intelligent polymer lenses, the maximum thickness of lenses is limited.

Advantageously, the present invention, through the use of an intermediate power in its relaxed state, enables the use of lower magnitude stimuli than prior art intelligent polymer lenses, and therefore allows for thicker lenses to be functional with lower magnitude stimuli than prior art and also allows for lower magnitude stimuli to produce the same difference in vision correction than the prior art.

Contact lenses of the present invention may be multi-focal, i.e. they may be able to take three or more shapes if required. In a preferred embodiment, the lens is adapted to form not only the shape when in the relaxed state as well as the first and second stimulated shapes, but also additional shapes. For example, when the first stimulus is emitted, the lens will take the first shape. However, if the magnitude of the first stimulus is reduced, but not eliminated, then the lens may take a shape between the relaxed state and the first stimulated shape, providing a milder visual effect than that provided by the first stimulated shape of the lens. The lens may be arranged such that the first and/or second stimuli are capable of being emitted in a range, meaning that a range of corrective optical powers may be provided. Alternatively, the stimuli may be emitted at fixed levels of magnitude meaning that the lens provides a fixed series of corrective optical powers.

For example, a contact lens in its relaxed state may have a corrective power of −3.00 D. Upon exposure to a stimulus, for example, a negative current, the lens changes shape and the change of corrective power may be −0.50 D, producing a corrective power of −3.50 D. An additional negative current may create a further change in corrective power of −0.50 D producing a distance contact lens shape which provides a corrective power of −4.00 D. Application of the opposite discrete stimulus may change the corrective power by +0.50 D and then a second input of current may cause an additional change in corrective power of +0.50 D, resulting in a lens shape which provides a corrective power of −2.00 D.

The lens when in the relaxed state and when in the first and second stimulated shapes may take any form provided that each shape, especially the first and second stimulated shape, provide different degrees of correction on the user's vision. The change in shape of the contact lens can be localised to the front surface and/or back surface and/or an embedded zone within the contact lens. Further a change of the embedded zone may either produce the required corrective power change on its own or create changes in the curvature of the front and/or back surface of the lens that produce all or part of the near addition to generate the required range of correction.

Regardless of whether the lens comprises an embedded zone or not, the lens may be provided with a cavity. The cavity preferably contains, and may be filled with gas, for example air. In embodiments where the lens does comprise an embedded zone, this may or may not be located in the cavity. Additionally or alternatively, the embedded zone may comprise a cavity of its own which preferably contains, and may be filled with gas, for example air. By providing a cavity in the lens, the magnitude of the stimulus required to obtain a corrective shape is significantly reduced.

This is illustrated if the corrective power of two lenses is compared at varying radii of curvature, where the first lens includes an embedded zone within the body of the lens and the second lens includes an embedded zone within an air-filled cavity.

For example, if the refractive index of the material making up the embedded zone is 1.39, the refractive index of the material making up the remainder of the lens is 1.37, the refractive index of air is 1.00, and the radii of curvature of the lenses in question are 10 mm and 9 mm, the following corrective powers would be obtained:

$$\text{Corrective Power }(D) = \frac{DIFFERENCE BETWEEN REFRACTIVE INDICES}{RADIUS OF CURVATURE(M)}$$

10 mm Radius of Curvature:

$$\text{First Lens: } \frac{(1.39 - 1.37)}{0.01} = 2.00D$$

$$\text{Second Lens: } \frac{(1.39 - 1.00)}{0.01} = 39.00D$$

9 mm Radius of Curvature:

$$\text{First Lens: } \frac{(1.39 - 1.37)}{0.009} = 2.22D$$

$$\text{Second Lens: } \frac{(1.39 - 1.00)}{0.009} = 43.33D$$

Thus, it can be seen that a 1 mm reduction in the radius of curvature causes a +0.22 D change in corrective power of the first lens (in which the embedded zone is present in the body of the lens), whereas the same reduction in the radius of curvature causes a +4.33 D change in corrective power of the second lens (in which the embedded zone is located in a cavity). Accordingly, the change in the degree of curvature (and thus the magnitude of the stimulus required) to achieve, say, a 1.00 D change in corrective power will be significantly higher for the first lens than for the second lens.

In certain embodiments, the first and second corrective, stimulated shapes may differ in terms of the degree of curvature of the lens. For example, the first shape may be highly curved and the second shape may only have a low degree of curvature.

Additionally or alternatively, the inner and/or the outer surfaces of the lens may change shape. This is preferable in arrangements where the lenses which are generally less curved or where a significant change in lens curvature is not acceptable, for example in intraocular lenses.

In a preferred embodiment of the present invention, the shape of the front surface changes shape to provide distance/near and/or any intermediate addition correction, while the back surface can be made toric to correct astigmatism. This arrangement is especially preferred when applied to contact lenses that are fitted on the front of the eye.

In an alternate preferred embodiment of the present invention, the shape of the back surface changes shape to provide distance/near and/or any intermediate addition correction, while the front surface can be made toric to correct astigmatism and/or aspheric to correct higher order aberrations.

In a further preferred embodiment of the present invention, where the lens comprises a gas-filled cavity with an embedded zone located therein, the shape of the front and/or back surfaces of the embedded zone change shape to provide distance/near and/or any intermediate addition correction, while the front and/or back surfaces of the overall lens can be made toric to correct astigmatism and/or aspheric to correct higher order aberrations. This arrangement is especially preferred when applied to intra ocular lenses.

The intelligent polymer may be incorporated in the lens in one or more intelligent polymer zones. In a preferred embodiment, the contact lens includes only a single intelligent polymer zone. In alternative arrangements, where a plurality of intelligent polymer zones are present, they preferably will all produce the same type of effect upon emission of the stimuli, e.g. they will all swell, or they will all shrink.

The first and second stimuli may independently be any trigger capable of causing shape change in the intelligent polymer, for example, temperature, pH, ionic strength, light, electric field, magnetic field, shear forces or a chemical trigger. However, it is envisaged that in most arrangements, the first and second stimuli will both be stimuli of the same type.

The first and second stimuli may differ in terms of their magnitude and/or polarity. For example, where the first and second stimuli are both electrical currents, the first stimulus may be a positive potential of a first magnitude and/or a range of magnitudes and the second stimulus may be a positive potential of a second magnitude and/or range of magnitudes. Alternatively, the first stimulus may be a positive electrical potential and/or a range of positive electrical potentials and the second stimulus may be a negative electrical potential and/or a range of negative electrical potentials or vice versa.

In arrangements where the first stimulus is positive and the second stimulus is negative, a further advantage is that any potential fatigue or lasting shape change in the intelligent polymer from repeated exposure to the first stimulus will be negated or at least reduced by exposure to the second stimulus For the purposes of the present invention, where the terms 'polarity', 'positive' and 'negative' are used in connection with the first and second stimuli, these terms are not only applicable to electrical or magnetic stimuli, where such terms would be conventionally used to describe properties of electrical or magnetic signals. They should also be applied to other types of stimuli. For example, if the stimuli are changes to pH, an increase of two pH units or subunits should be described as a positive stimulus and a decrease of two pH units or subunits should be described as a negative stimulus, of opposing polarity to the first stimulus.

Contact lenses of the present invention may be formed in their entirety of intelligent polymer. Alternatively, they may be partly formed of conventionally used lens material including a region formed of intelligent polymer. In one arrangement, the responsive polymer will only comprise the optical zone and/or will be embedded in the contact lens and/or constitute all or part of the anterior or posterior of the contact lens.

Any suitable responsive polymer gel which changes shape may be used in the present invention. The polymer gel is preferably compatible with ocular tissue. If the polymer gel is not compatible with ocular tissue, it may be included within the contact lens to avoid direct interaction between the polymer and the ocular tissue. Particularly preferred are those which will change shape under changes in environmental conditions and/or when a stimulus such as an electric or magnetic field is applied. The polymer may also undergo a change in refractive index.

Examples of polymers that may be employed in the lenses of the present invention (inside and/or outside regions of intelligent polymer) include hydrogels, silicone hydrogels, silicone polymers, poly(urethanes), poly(siloxanes), silicones, poly(methyl methacrylate), poly(vinyl alcohol), poly(ethylenes), poly(vinyl pyrrolidone), poly(methacrylic acid), poly(acrylamide), poly(ethylene oxide), poly(acrylic) acid, poly(propylene oxide), and poly(2-hydroxy ethyl methacrylate) or mixtures thereof.

Intelligent polymers that may be included in lenses of the present invention which are partially or totally stimulated by electrical impulses are preferably electronic electrically activated polymers (polymers that change shape or dimensions due to migration of electrons in response to electric field) or ionic electrically activated polymers (polymers that change shape or dimensions due to migration of ions in response to electric field). As those skilled in the art will be aware, electronic EAPs are usually dry polymers and ionic EAPs are typically wet and/or include electrolytes. However, where used in the lenses of the present invention, those EAPs are not necessarily so limited.

Examples of electronic EAPs which may be employed in the lenses of the present invention include dielectric EAPs (e.g. silicone and acrylic elastomers such as acrylic elastomer VHB 4910), electrostrictive elastomers (e.g. polyurethane elastomers, silicon rubber and electrostrictive grafted elastomers such as flexible backbone polymer grafted with crystalline group/s), electro-viscoelastic elastomers (e.g. silicon elastomer and semi conducting polymer particles), piezoelectric polymers, ferroelectric polymers (e.g. polyvinylidene fluoride (PVDF) and poly[(vinylidenefluoride-co-trifluoroethylene] [P(VDF-TrFE)]) and/or carbon nanotube aerogel or mixtures thereof.

Examples of ionic EAPs which may be employed in the lenses of the present invention include polymer gels (e.g. polyacrylic acid, polyvinyl alcohol, modified polyacrylonitrile), polyelectrolyte materials, ionic polymers (optionally including metal composites), ion-exchange polymer metal matrix composites (IPMC) (e.g. ion exchange polymer and gold plating), electro conducting conjugated polymer (e.g. polypyrrole, polyaniline) and/or carbon nanotubes or mixtures thereof.

Examples of natural or synthetic polymers can be used to prepare responsive materials and specific examples include chitosan, chondroitin sulfate, hyaluronic acid, and alginate, vinyl alcohol, allylamine, acrylonitrile, 2-acrylamido-2-methypropane sulfonic acid, aniline, 2-hydroxyethyl methacrylate, methacrylic acid, acrylic acid, vinyl sulfonic acid, poly(2-hydroxyethyl methacrylate) and chitosan, poly(vinyl alcohol) and poly(sodium maleate-co-sodium acrylate), alginate/poly(diallyldimethylamomium chloride), acrylic acid/vinyl sulfonic acid hydrogel, hydrogel based on polyacrylic acid/polyvinyl sulfonic acid, poly(acrylic acid)-co-(acrylamide) gels, acrylic acid acrylamide copolymere gels PAAm, poly(vinyl alcohol)-poly(acrylic acid) gels, poly(vinyl alcohol)-poly(sodium acrylate), polyacrylic acid with sodium acrylate crosslinked with bisacrylamide, polyacrylonitrile, polysodium acrylate (PAANa), Gelatin/poly(hydroxyethylmethacrylate) hydrogel, polyelectrolyte gels as vinyl polymer and polyelectrolyte (hyaluronic acid), and poly(dimethyl siloxane) with $TiO_2$ particles, or mixtures thereof.

Other examples of components that can be used in the preparation of responsive materials include magnetite, ferrogels, metallic (e.g. titanium dioxide) particles and/or plating, metal composite particles and/or plating, semiconducting polymer particles, polyN-isopro-pylacrylamide poly (hydroxyethyl methacrylate), styrene-ethylene/butylene-styrene triblock polymer gels, ethylene vinyl alcohol, and/or other polyelectrolytes or additives, or mixtures thereof.

In certain aspects of the present invention, additional additives known to those skilled in the art may be employed in the lenses of the present invention (inside and/or outside regions of intelligent polymer present in the lens). Examples of additional additives include one or more of initiators, surfactants, wetting agents, colouring or pigmentation agents, crosslinkers (e.g glutaraldehyde), or mixtures thereof.

One problem experienced by the users of prior art intelligent polymer lenses is the slow response time, i.e. the time that elapses between emission of the stimulus and the corrective shape being achieved. For example, in WO2006/055707, response times of 0 to 15 seconds were observed. There is a need for the provision of lenses which are capable of providing corrective shapes within subsecond response times. Thus, in one preferred embodiment of the present invention, the lens exhibits a first response time (the time taken for the lens to move from the relaxed state to the first corrective shape upon emission of the first stimulus) and/or a second response time (the time taken for the lens to move from the relaxed state to the second corrective shape upon emission of the second stimulus), independently, of about 1 second or less, more preferably about 0.8 seconds or less, about 0.6 seconds or less, about 0.5 seconds or less, about 0.4 seconds or less, about 0.3 seconds or less, about 0.2 seconds or less, about 0.1 seconds or less, or about 0.05 seconds or less.

Additionally or alternatively, the lens of the present invention preferably has a first relaxation time (the time taken for the lens to revert to the relaxed state from the first corrective shape upon cessation of the first stimulus) and/or a second relaxation time (the time taken for the lens to revert to the relaxed state from the second corrective shape upon cessation of the second stimulus), independently, of about 1 second or less, more preferably about 0.8 seconds or less, about 0.6 seconds or less, about 0.5 seconds or less, about 0.4 seconds or less, about 0.3 seconds or less, about 0.2 seconds or less, about 0.1 seconds or less, or about 0.05 seconds or less.

As will be appreciated from this description of the present invention, one of the main aims of the invention is to provide a lens which is capable of repeatedly and reliably reverting to its original, relaxed state rapidly, following cessation of the first or second stimuli. One of the main advantages of the present lens is its resistance to fatigue, i.e. where, after having been repeatedly held in one corrective shape for extended periods of time, the lens is incapable of returning fully to its relaxed, natural shape. Accordingly the use of shape-memory intelligent polymers (which are designed to attain a shape upon exposure to a first stimulus and partially or totally retain their shape once emission of the stimulus has been ceased) is not preferable in the present invention. Thus, the intelligent polymer employed in the lens of the present invention preferably comprises less than about 50% shape-memory polymer, less than about 20% shape-memory polymer, less than about 10% shape-memory polymer, less than about 5% shape-memory polymer, or most preferably, less than about 1% shape-memory polymer.

As mentioned above, the term 'contact lens', in the context of the present invention is used to refer to a variety of lenses, including onlay and inlay lenses. Inlay and onlay lenses are suitable for implantation in the anterior stroma or just below the corneal epithelium. Inlay and onlay lenses generally have a constant shape that differs from the shape of the cornea; for those lenses which correct myopia, the shape is less curved than the cornea and for those which correct hyperopia, the shape is more curved than the cornea. It is also possible to correct astigmatism by employing onlay or inlay lenses with different curvatures in different directions introducing both a spherical and an astigmatic correction.

In embodiments of the present invention, inlay or onlay lenses will be formed, at least partially, from intelligent polymer and will be capable of changing shape upon exposure to the first and second stimuli and/or range of stimuli.

One advantage which is provided through the use of inlay or onlay lenses is that the lens will be placed in the eye by an ophthalmic surgeon and will therefore not need a stabilisation system to perform.

The stimuli for changing the shape of the contact lens can be provided by the ocular environment around the contact lens or alternatively by any artificial means within the contact lens.

The device may include a detector and separately a device for causing the stimuli.

In one arrangement, a device embedded in one or both contact lenses will produce localised changes that will trigger the responsive polymer to reversibly change from the relaxed state to a first, second, or any additional corrective, stimulated shapes.

The first and second stimuli for changing the shape of the contact lens surfaces or the shape of an embedded part of the lens may be provided by an electric field produced by means embedded in the contact lens itself. Any suitable means for providing the electric field may be used. In one arrangement a chip may be embedded in the contact lens. The chip may be a nano or micro chip and will generally be configured so that it is not visible to the user. The chip may be triggered to emit the electric stimuli by any suitable means.

The stimuli for changing the shape of the contact lens surfaces or the shape of an embedded part of the lens may be provided by a magnetic field produced by stimuli emission means embedded in the contact lens itself. Any suitable means for providing the magnetic field may be used. In one arrangement a chip may be embedded in the contact lens. The chip may be a nano or micro chip and will generally be configured so that it is not visible to the user. The chip may be triggered to emit the magnetic field by any suitable means.

In preferred arrangements, the contact lens of the present invention comprises a power source. This may be used to emit the first and/or second stimuli directly to the lens. Alternatively, the power source may be used to drive stimuli emission means. For example, where the stimuli used to drive the lens from the relaxed state to the first or second corrective shapes are magnetic fields, the power source may be configured to power an electromagnet which, when supplied with electricity emits the first or second stimuli. Alternatively, where the stimuli emission means is a chip embedded in the lens, the power source may be configured to provide electricity to the chip, which will then emit an electrical charge of the correct magnitude. Alternatively, the chip may be configured to also function as a power source.

The power source may be of any type capable of delivering the appropriate amount of electrical energy to result in the lens being moved from its relaxed state to its first and second corrective shapes, either directly or indirectly. In preferred embodiments, the power source is a chemical cell, a pre-charged cell, a cell capable of harvesting energy from the environment (e.g. solar powered) and/or the human body.

In an especially preferred embodiment, the power source is partially or totally embedded within the lens. This is advantageous as the user is not obliged to ensure that ancillary power supplies are kept in their possession while the lens is being worn. In a most preferred embodiment, the lens is completely self-contained, i.e. all components of the lens which are necessary for its operation are partially or totally embedded within the lens.

The contact lens of the present invention preferably comprises means for monitoring eye movement. In preferred arrangements, a micro or nano chip functions to monitor eye movement. The same or different chips may be used to emit stimuli and monitor eye movement.

In one arrangement, the chip will monitor the eye movement and a change in eye movement will cause the chip to emit the stimulus required to cause the responsive polymer to change to the first or second corrective shape as necessary. The monitoring of the eye movement may be carried out by the chip itself or by a separate detector in communication with the chip.

For example, the chip may be triggered when the user gazes inwardly and the lens may be changed from the relaxed state to the first corrective shape, which in preferred embodiments, provides a near addition correction, allowing the user is able to clearly focus on close material. When the user then gazes towards distant objects, emission of the first stimulus may be ceased, and the second stimulus may be triggered, causing the lens to change from the first shape, transiently to the relaxed state and then to the second shape, which, in preferred embodiments provides a distance correction.

In one alternative arrangement, the chip or a separate detector may identify the inter-pupillary distance which is the distance between the pupils of the right and left eye. When the user is looking straight ahead, the distance between the two eyes is at its maximum. In one arrangement, it would be desirable for the chip to emit the second stimulus, to cause the lens to change to the second shape which preferably provides a distance correction. When the user then looks at a point that is closer to them, the pupils of their eyes move closer together and this will be detected. The chip will react to the change in distance and this will trigger the emission of the first stimulus causing the lens to change from the relaxed state to the first shape, which preferably provides a near addition correction and will allow the user to focus on the point which is closer to them.

In a more preferred embodiment, if the user were to look at still closer points, causing their eyes to come closer together, the magnitude of the first stimulus produced by the chip will change to give a proportional change in the shape of the contact lens which will alter the power of the lens.

Additionally or alternatively, the chip will monitor the relative distance of a pair of contact lenses. When the user passes from distance gaze to near distance gaze, the contact lenses move with the eye and get closer together, hence tracking the distance between the two contact lenses. The change in relative distance between the two contact lenses will produce either continuous or discrete changes in the magnitude of the second stimulus proportional to the degree of distance correction needed to allow the user to continually focus on the point of interest.

Thus in a most preferred arrangement, the contact lens will provide an exact correction for all focusing distances. This is particularly possible with responsive polymers which have a reaction time that is sufficiently fast that the change is not noticeable by the user so they experience clear vision at all time.

In an alternative preferred arrangement, instead of the magnitude of the first and second stimuli being varied proportional to the degree of correction required, the lens will be arranged such that first and second stimuli of predetermined magnitude are emitted as and when required.

Additionally to the first and second stimuli resulting in a change in shape, the stimuli may induce a change in refractive index.

Lenses of the present invention advantageously produce the correct corrective power for the distance at which the eye is directed at any one moment (e.g. distance vision while driving, intermediate vision while looking at the dash board or near vision when reading a map.)

To enable this adjustment in corrective power to be effected, the lens must be able to detect the distance of the object of interest. This can be achieved by measuring the relative distance between the two contact lenses or alternatively the interpupillary distance. As contact lenses move with the eyes and the distance between the two eyes decreases in a linear mode when looking from far distance to near in a predictable manner, the distance between the lenses should be indicative of the distance of the object being viewed.

However, a disadvantage of this system is that the difference in distance between the two contact lenses or the two eyes between distance vision and near vision depends upon the position of the contact lens in the eye in relation to the centre of rotation of the eye. The distance from the cornea to the centre of rotation of the eye has been reported to range from 12.95 mm to 14.73 mm (Park RS and Park GE, 1933). In the case of corneal contact lenses or corneal onlay or inlay lenses, the same difference applies to the centre of rotation of the eye. When looking from far to near, for example at 40 cm, the change in distance between the two corneal contact lenses or corneal onlays or inlays is between 2.08 mm and 2.36 mm. However in the case of a intraocular lens which is positioned 2 mm in front of the centre of the eye, the change in distance is very small and of the order of 0.32 mm because the lens in located near or at the centre of rotation of the eye.

In one arrangement, in order to offset the above-mentioned problem, a chip may be employed which will monitor the eye movement (eye rotation). A change in eye movement (relative rotation) will cause the chip to emit a stimulus required to cause the responsive polymer to change to the first or second or any corrective, stimulated shape as necessary. The chip itself, or a separate detector in communication with the chip may monitor eye movement.

When the eyes are directed towards a distant object (sometimes referred as infinity) the lines of sight (the line between the object that is looked at and the foveal part of the retina where detailed vision takes place) of the two eyes are parallel (relative angle 0°). When the eyes are directed at an object closer than infinity, the eyes are turning in; the relative angle between the lines of sights changes in as a pair. This rotational movement of the eye is known as convergence. For a pair of eyes separated by a given distance when looking at infinity, there is a direct relationship between the distance of visual interest at which the contact lens should focus and the angle between the line of sight of the two eyes, also known as the convergence angle.

The change in eye convergence can be used as the trigger for emission of the stimulus to produce a change in shape of the contact lens in part or overall. This provides several advantages. Firstly, the differences to detect are relatively large. For example for a pair of eyes where the distance between the lines of sight while looking at infinity is 64 mm, the angle of convergence between the two lines of sight changes from 0° (at infinity) to 9.1° (for a reading distance of 40 cm). A further advantage is that the angle of the line of sight does not depend upon the relative position of the lens with reference to the centre of rotation as long as it is not at the centre of rotation. Hence, the system is as efficiently applicable to the any of the lenses described here including intraocular lenses.

Because the contact lenses rotate with the eye the trigger can alternatively be produced by the relative tracking of the rotation of the two contact lenses.

As a further aspect of the present invention, there is provided a pair of lenses which are substantially as described above. In especially preferred embodiments, the pair of lenses are self-contained, meaning that all components necessary for their operation (including, for example, means to enable them to detect the respective distance between them, from which the interpupillary distance can be determined) are partially or totally embedded in the lenses, meaning that there is no obligation on the user to carry ancillary components of the lens system in order for the lenses to correctly operate.

According to a still further aspect of the present invention, there is provided a kit comprising one or more pairs of lenses as described herein. The kit preferably further comprises instructions for use of the lenses.

The invention is further illustrated in the figures which will be discussed below, followed by examples.

FIGS. 2 to 13 illustrate a range of embodiments of the present invention. The rotational and radial positions of all of the components shown in the exemplified arrangements are illustrative and may be located at any position within the lens. The stabilisation features shown in the exemplified arrangements are located in the lower part of the contact lenses for illustrative purposes only; they represent all types of stabilisation methods applicable to contact lenses. Additionally, in the illustrated embodiments, a circular wire is used to transmit electrical energy throughout the cell. However, the lenses of the present invention are not so limited; any type of means of any type of shape which achieve the transmission of the stimulus/stimuli throughout the lenses of the present invention may be employed.

Figure 2:
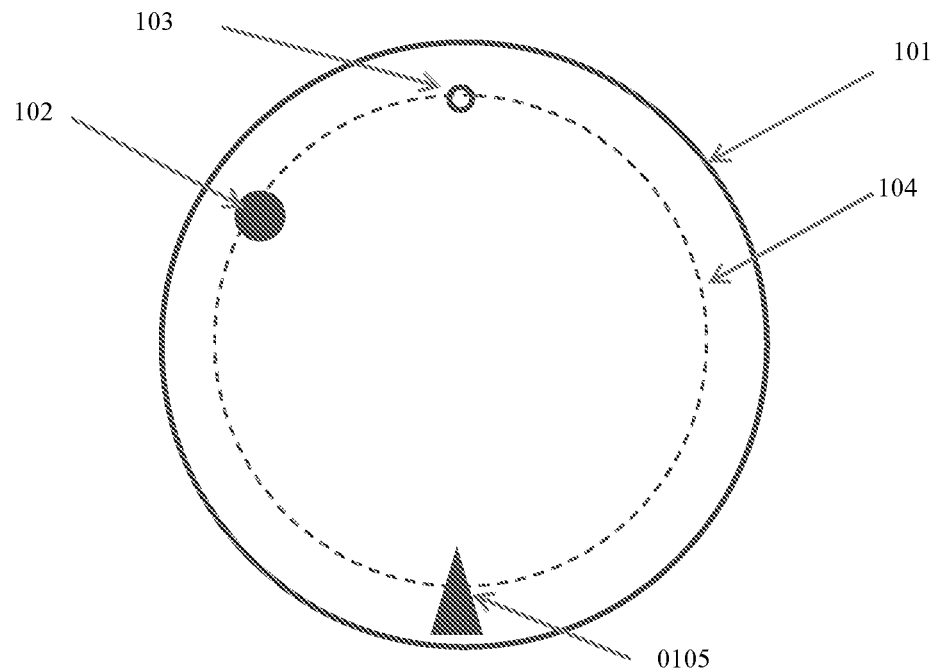
FIG. 2 shows right and left responsive gel contact lenses.
Figure 2:
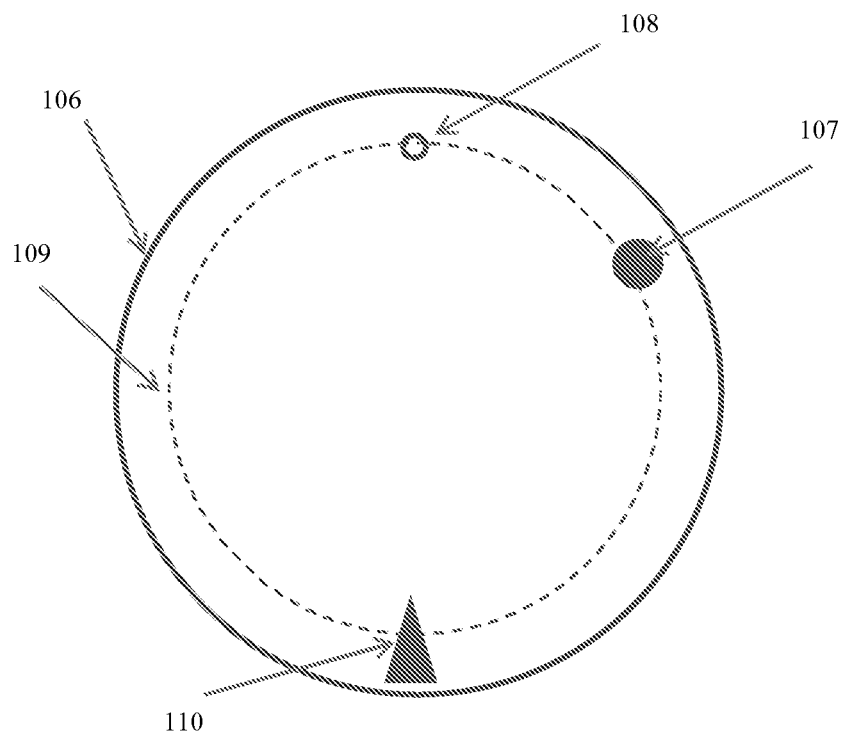

FIG. 2 shows right and left responsive gel contact lenses 101, 106 which both are powered by solar powered cells 102, 107. The solar cells 102, 107 are connected to wires 104, 109 which serve to connect the cells to the other components included in the lenses and also to supply electrical stimuli to the lenses. The emission and magnitude of the stimuli are controlled by chips 103, 108 which also receive emit and receive signals regarding the relative position of the lenses with respect to each other. The lenses are also provided with stabilising features 105, 110.

In general terms, lenses configured in this way operate by emission of an electrical stimulus when an appropriate signal is received by the chips 103, 108. The chip then triggers release of the electrical stimulus to the wire, which carries the stimulus to the body of the lens. The intelligent polymer from which the lens is formed then changes shape.

Of course, other stimuli may be employed and, where the stimulus is an electrical current, other types of power supply than solar cells may be used.

Figure 3:
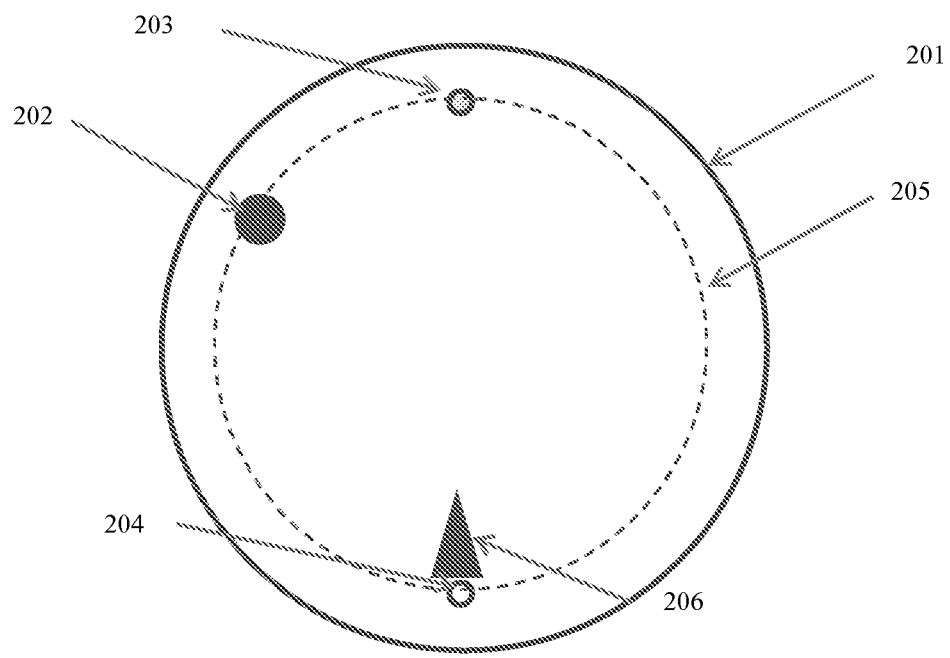
FIG. 3 shows an alternative configuration in which a pair of chips is used in each lens to receive and emit signals regarding the relative position of the lenses.
Figure 3:
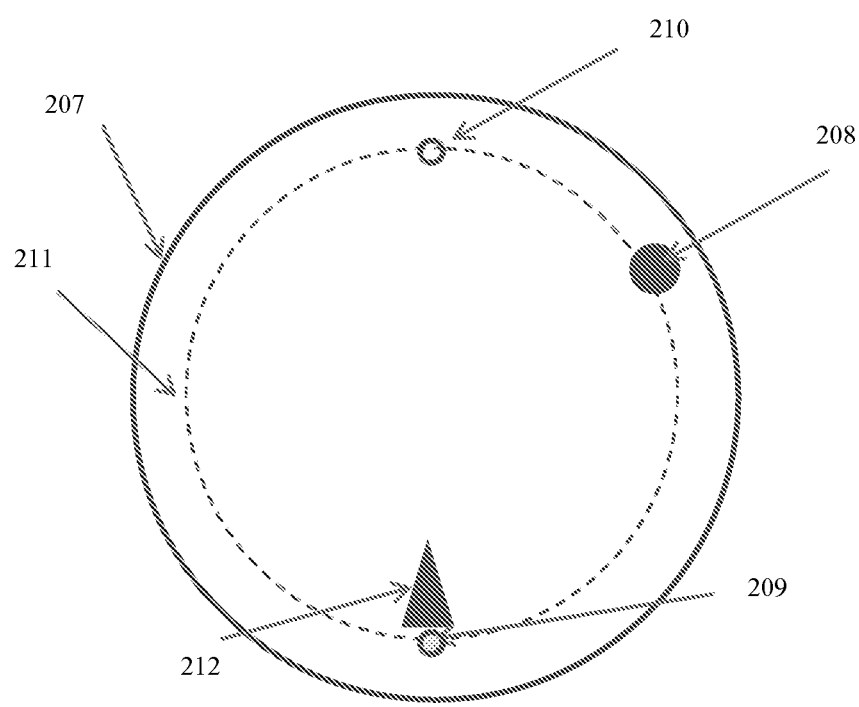

FIG. 3 shows an alternative configuration in which a pair of chips is used in each lens to receive and emit signals regarding the relative position of the lenses. More specifically, a first chip 203, 210 receives signals and a second chip 204, 209 emits signals. Additionally, unlike the arrangement shown in FIG. 2, the chips 203, 204, 209, 210 are not responsible for controlling the output of electric stimuli; this role is fulfilled by the cells 202, 208. The wires 205, 211 and stabilising features 206, 212 operate in the same way as in the lenses shown in FIG. 2.

Figure 4:
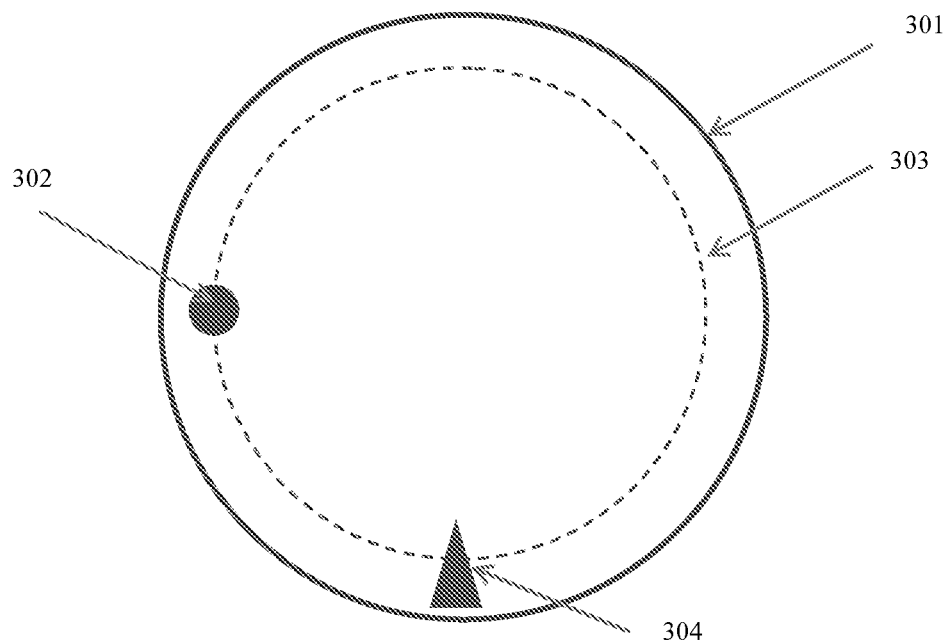
FIG. 4 shows a simplified configuration of lenses.
Figure 4:
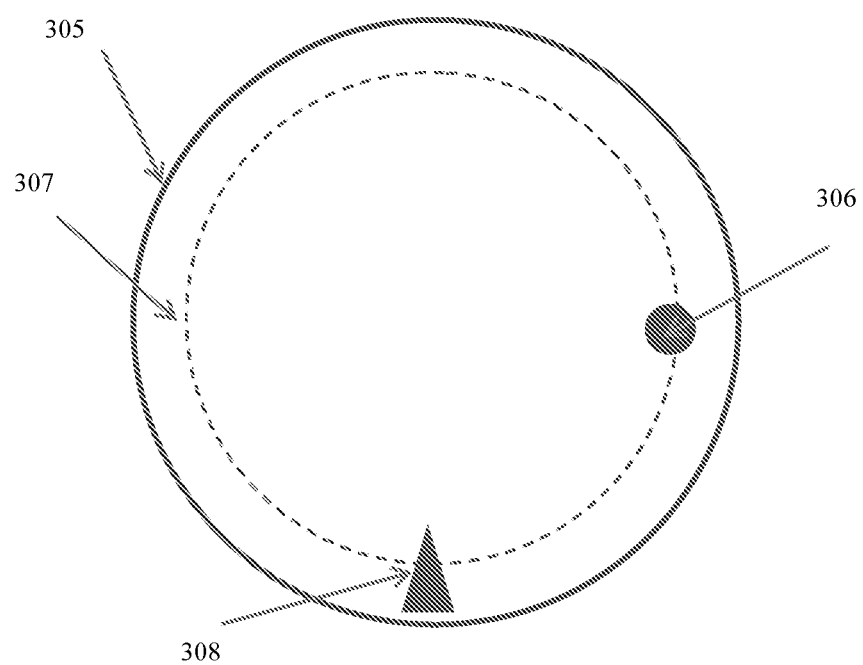

The configuration shown in FIG. 4 is simplified. A single component 302, 306 fulfils the role of both the cells and the chips discussed above. The wires 303, 304 and stabilising features 307, 308 operate in the same way as in the lenses discussed above.

Figure 5:
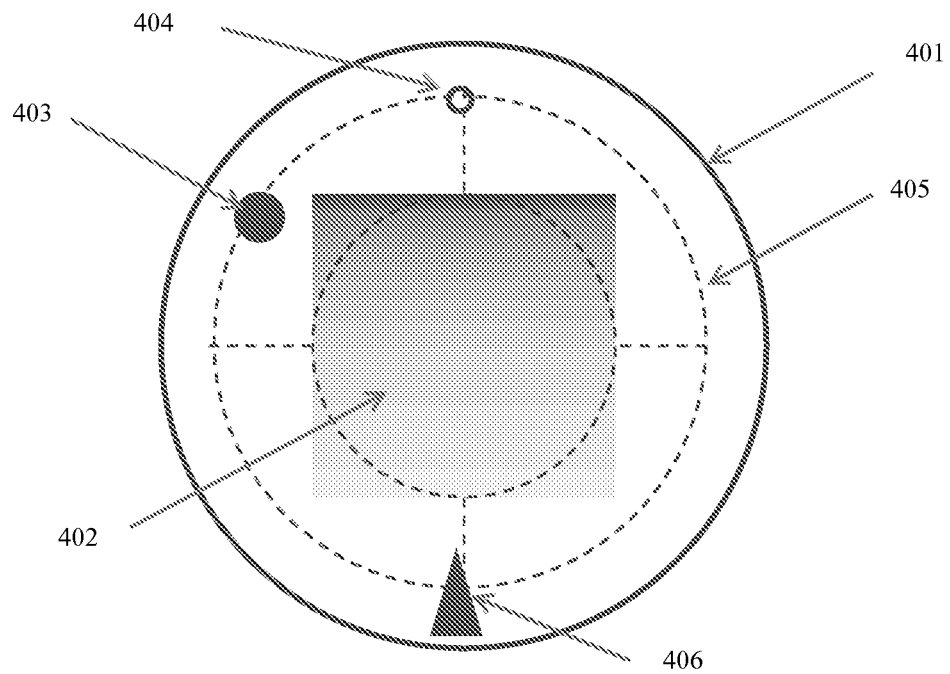
FIG. 5 shows lenses that are not formed completely of intelligent polymer but include inserts formed from that material.
Figure 5:
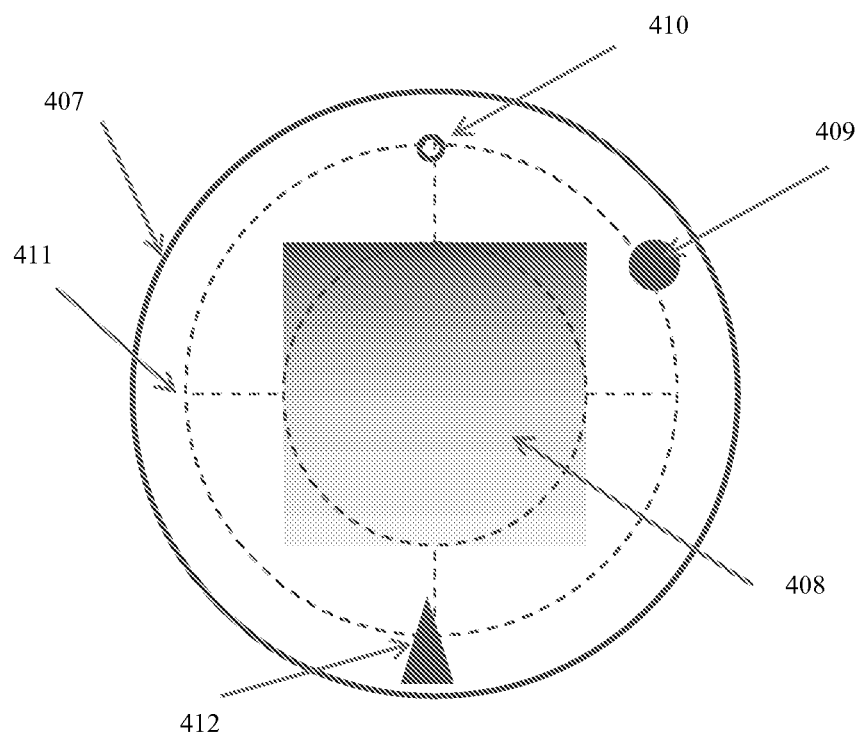

Unlike the configurations depicted in FIGS. 2 to 4, the lenses 401, 407 shown in FIG. 5 are not formed completely of intelligent polymer, but only include inserts 402, 408 formed from that material. To ensure that the stimuli reaches the inserts 402, 408 a more complex wire network 405, 411 is required. The chips 404, 410 emit and receive signals regarding the relative position of the lenses with respect to each other and also control emission and the magnitude of electrical stimuli from the cells 403, 409

Figure 6:
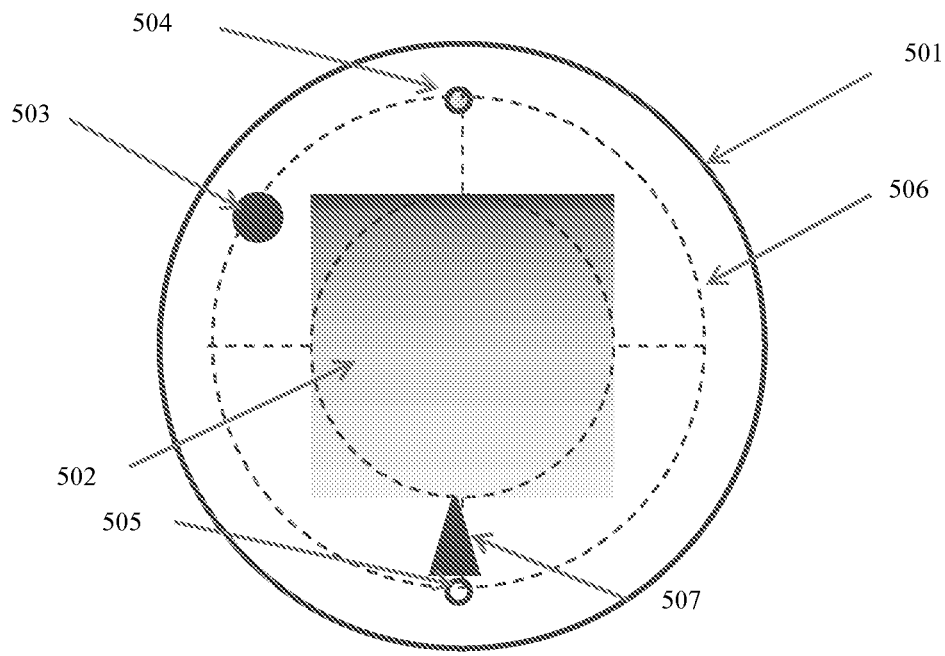
FIG. 6 shows lenses of including intelligent polymer inserts and a pair of chips responsible for emitting and receiving signals regarding the relative position of the lenses, respectively.
Figure 6:
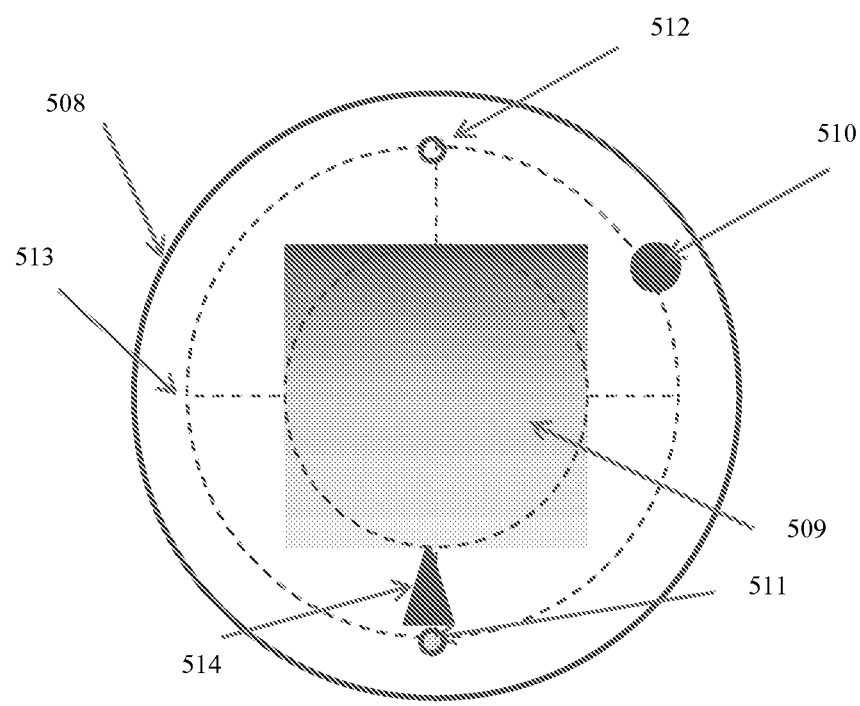

The lens configuration shown in FIG. 6 is similar to that depicted in FIG. 5 in that the lenses 501, 508 include intelligent polymer inserts 502, 509. The only difference is that a pair of chips 504, 511, 505, 512 is responsible for emitting and receiving signals regarding the relative position of the lenses, respectively. The chips which receive the position signals 505, 512 are also responsible for controlling the emission and the magnitude of electrical stimuli from the cells 503, 510. The wires 506, 513 and stabilising features 507, 514 function in the same way.

Figure 7:
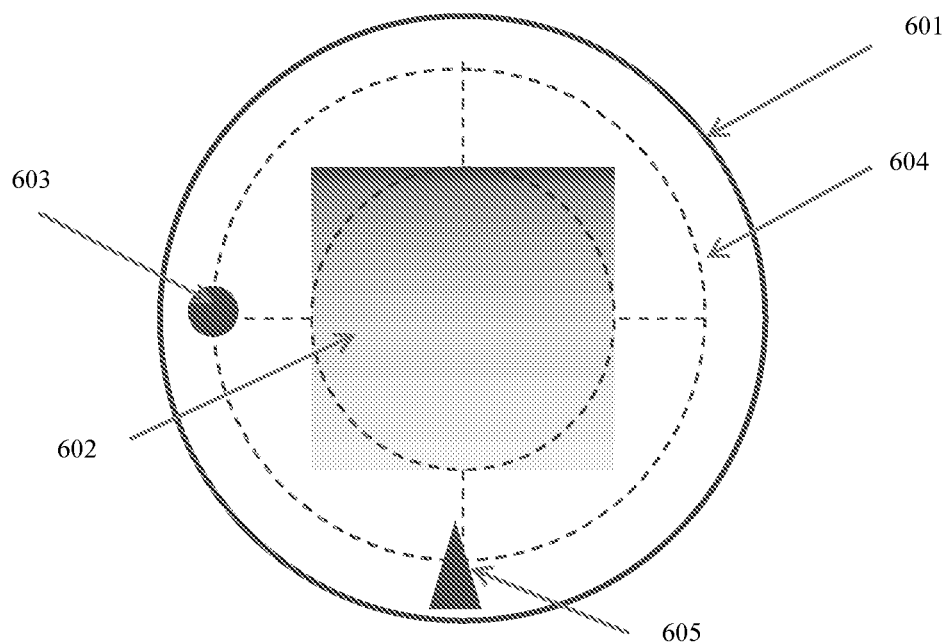
FIG. 7 shows a lens pair with single components fulfilling the roles of the chips and the cells disclosed herein.
Figure 7:
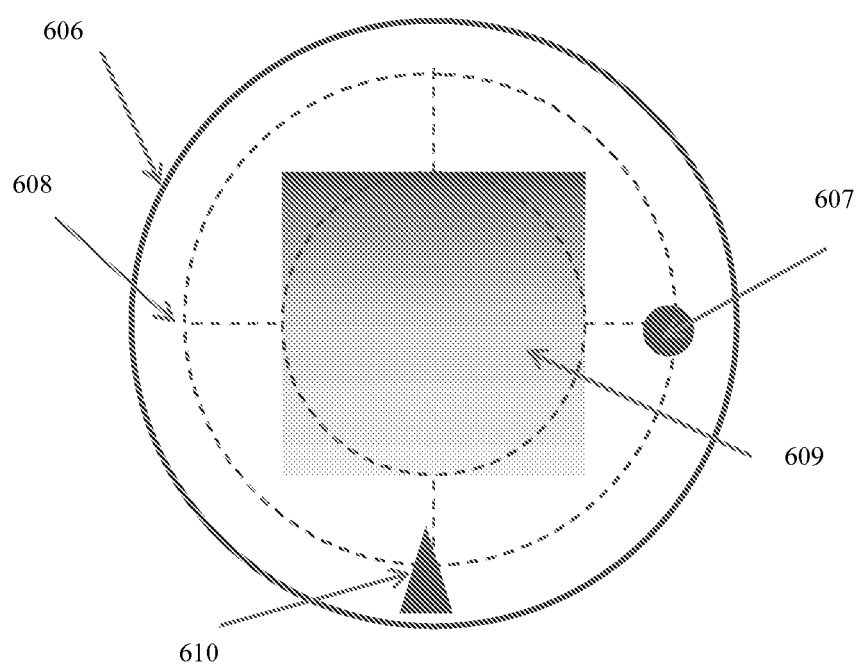
Figure 8:
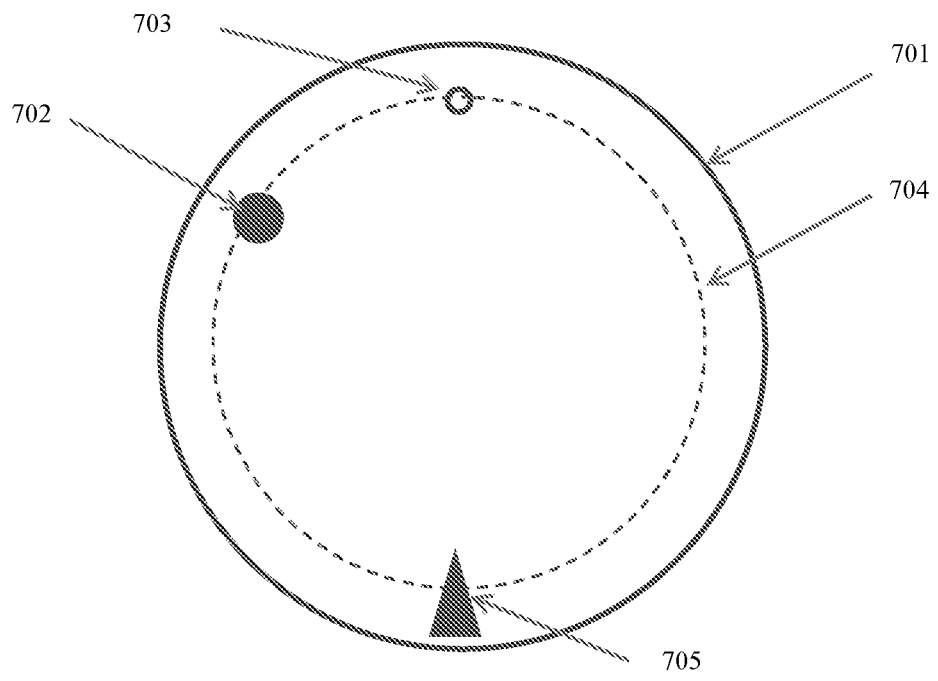
FIGS. 8 to 13 show configurations which conform to those shown in FIGS. 2 to 7, except that the chips 708, 809, 906, 1010, 1111, 1207 included in the left lenses 706, 807, 905, 1007, 1108, 1206 do not emit signals regarding the relative position of the lenses with respect to each other. This role is solely fulfilled by the chips 703, 804, 902, 1004, 1104, 1203 included in the right hand lenses 701, 801, 901, 1001, 1101, 1201.
Figure 8:
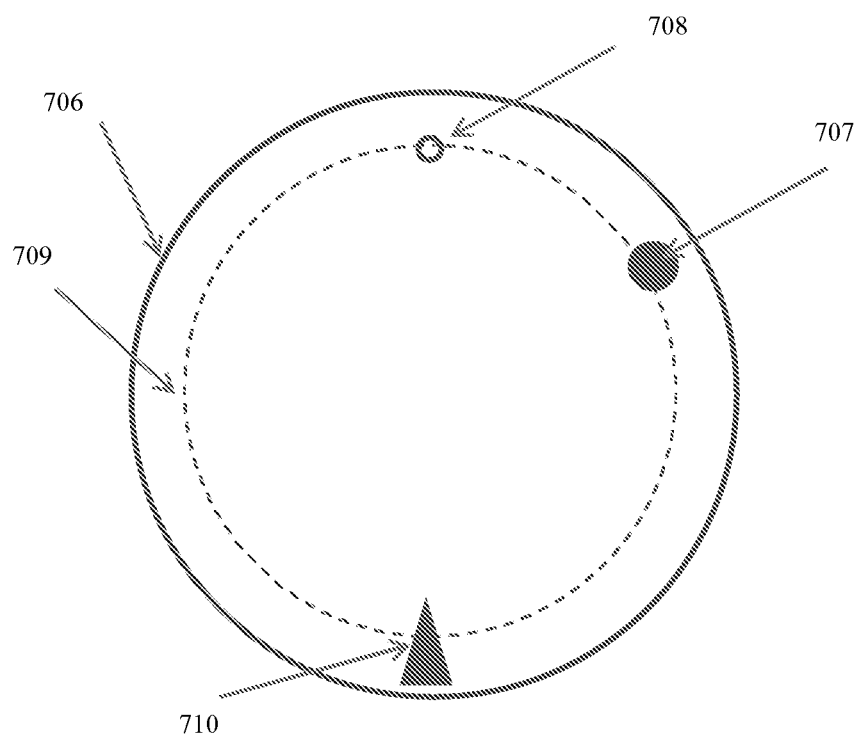
Figure 9:
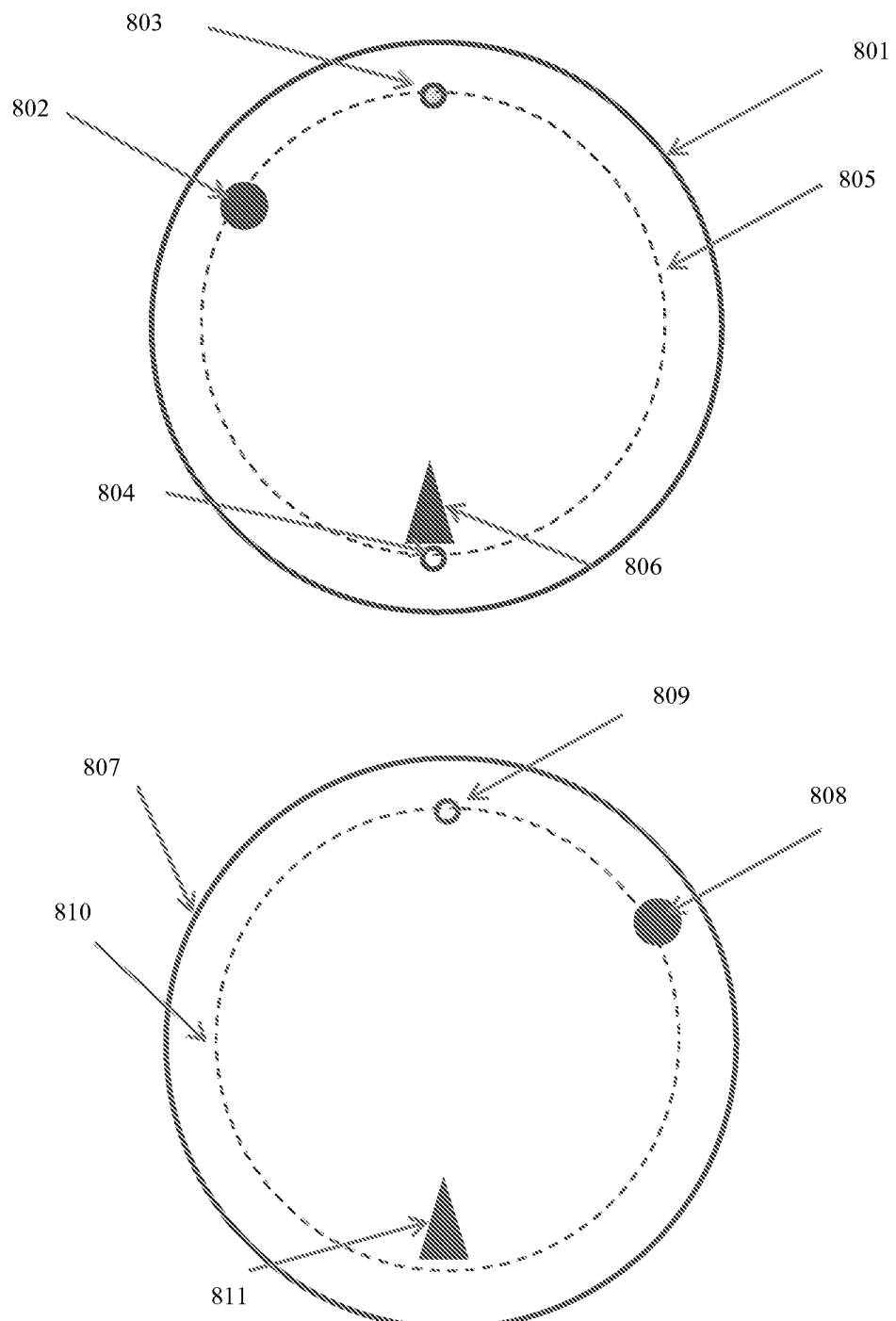
Figure 10:
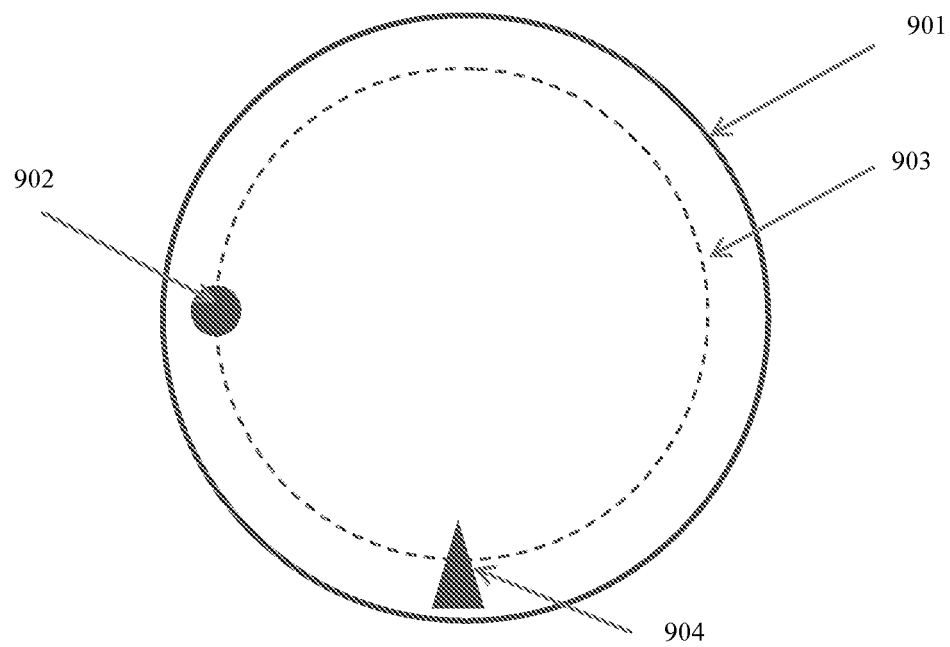
Figure 10:
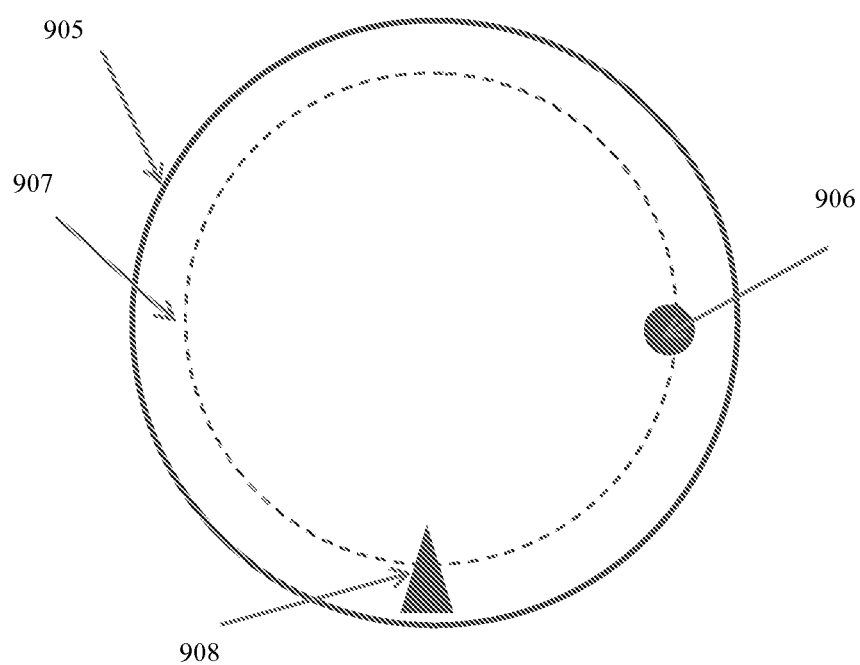
Figure 11:
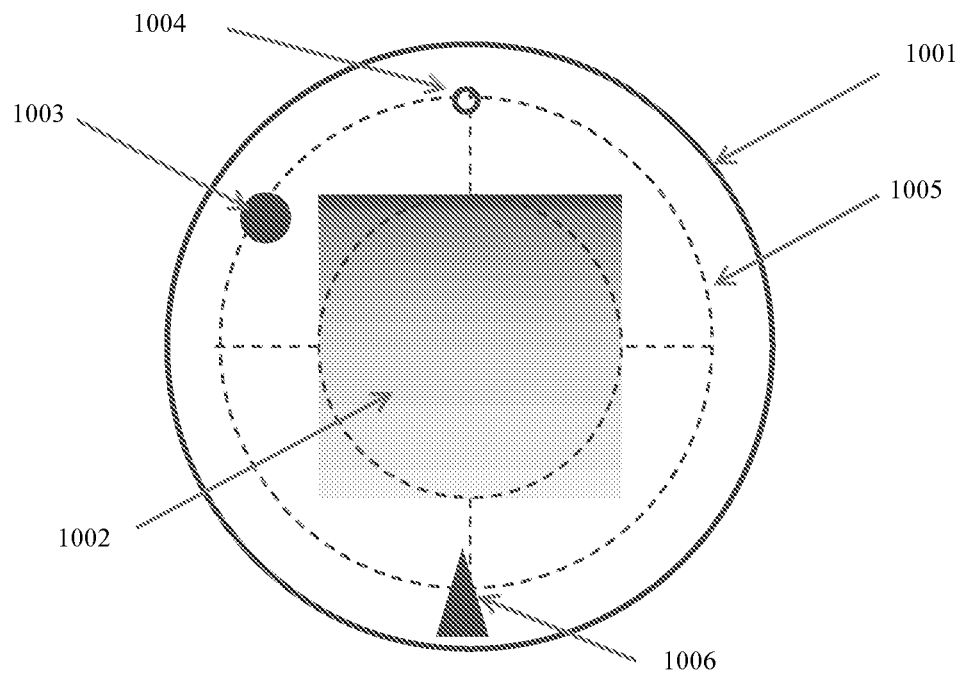
Figure 11:
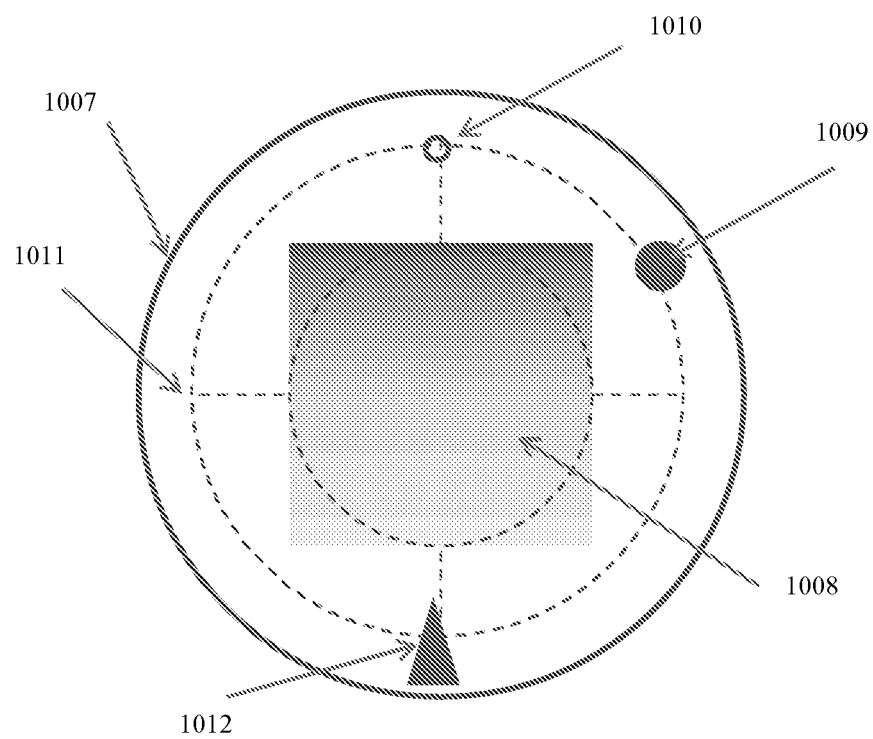
Figure 12:
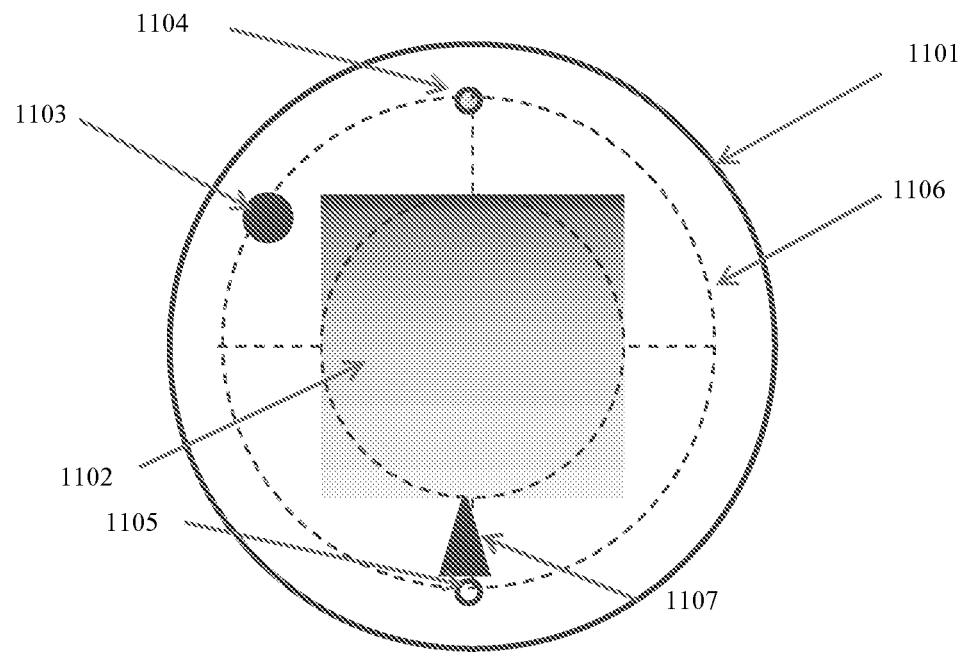
Figure 12:
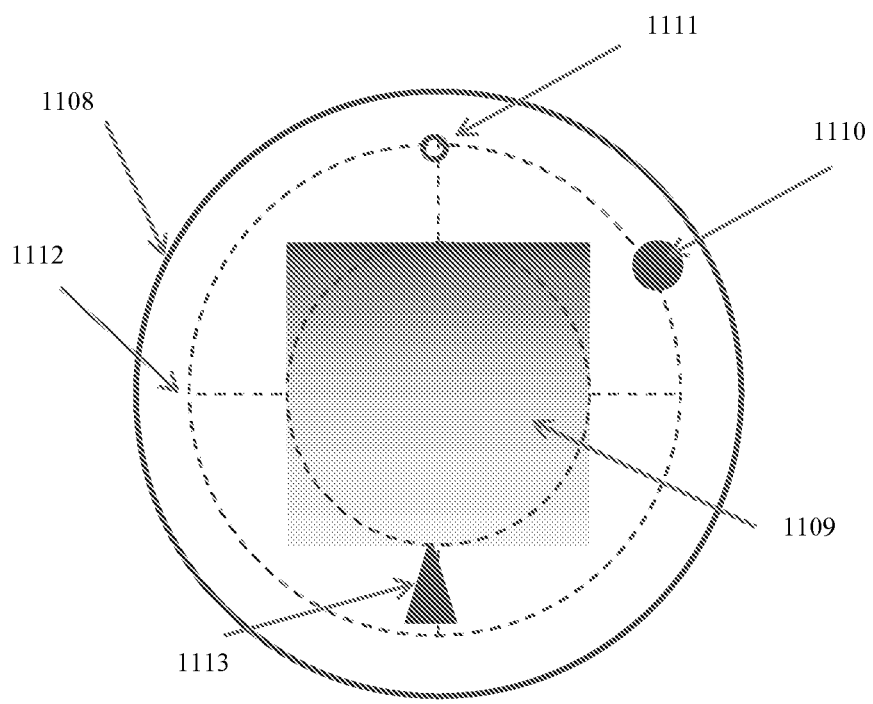
Figure 13:
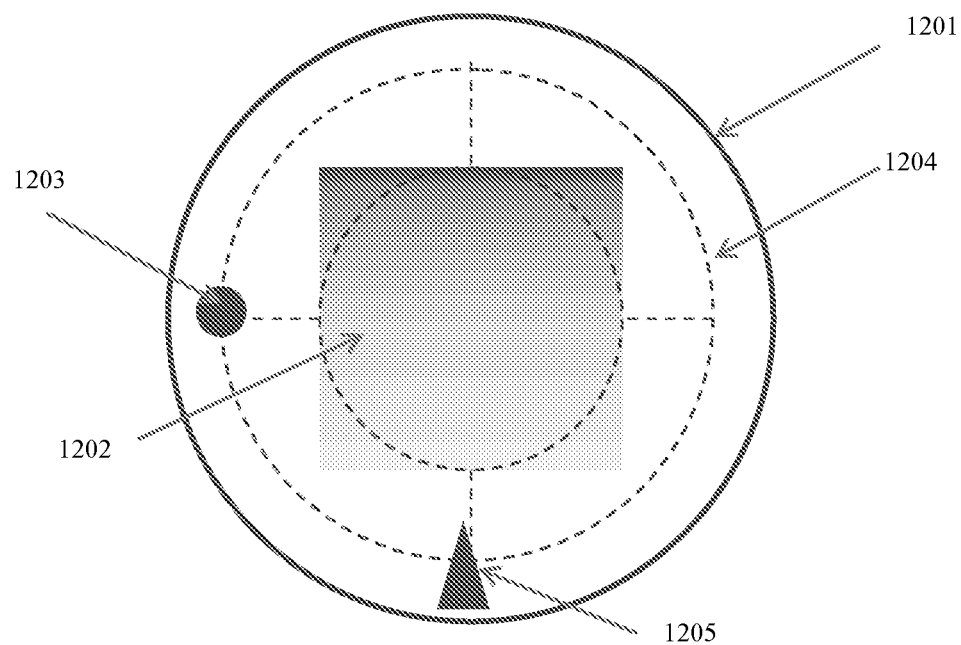
Figure 13:
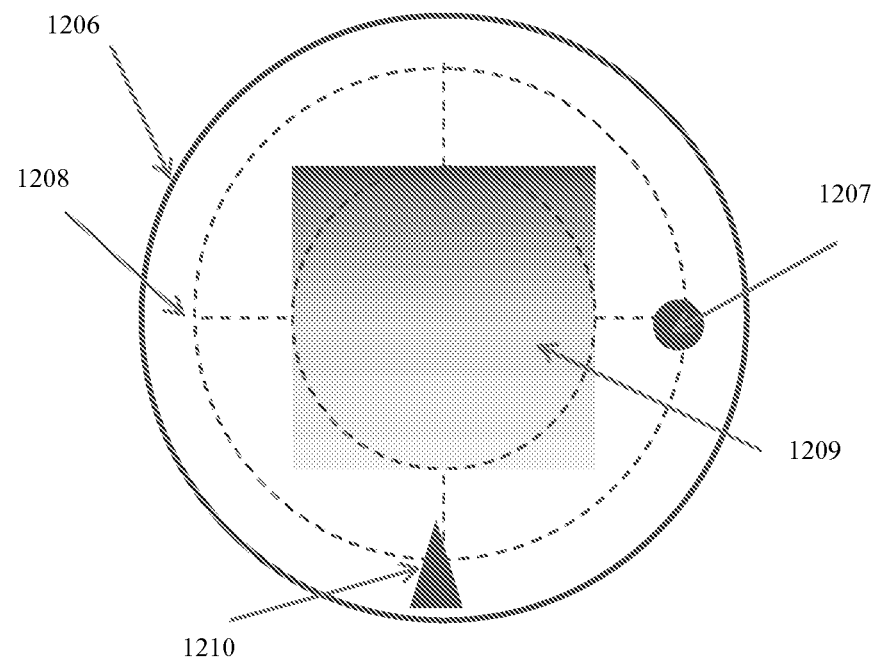

FIG. 7 depicts a lens pair 601, 606 which is similar to that shown in FIG. 4 in that single components 603, 607 fulfil the roles of the chips and the cells discussed above. The illustrated arrangement differs from that of FIG. 4 in that the lenses 601, 606 include intelligent polymer inserts 602, 609. The wires 604, 608 and stabilising features 605, 610 function in the same way.

FIGS. 8 to 13 depict configurations which conform to those shown in FIGS. 2 to 7, except that the chips 708, 809, 906, 1010, 1111, 1207 included in the left lenses 706, 807, 905, 1007, 1108, 1206 do not emit signals regarding the relative position of the lenses with respect to each other. This role is solely fulfilled by the chips 703, 804, 902, 1004, 1104, 1203 included in the right hand lenses 701, 801, 901, 1001, 1101, 1201.

For the avoidance of any doubt, the following table identifies which reference numerals correspond to the features shown in FIGS. 8 to 13:

EXAMPLES

The foregoing arrangements may be operated in the manner now described. For simplicity the examples are described with reference to the arrangement shown in FIG. 2.

For the avoidance of any doubt, where the term "proportional" is used, this does not necessarily mean that the magnitude of the stimulus is truly proportional to the difference between the respective degrees of separation or angles of convergence discussed below. The term may be used to convey a general positive or negative relationship therebetween.

Where 'X', 'Y' and 'Z' are used below to quantify stimuli, 'X' is a stimulus having a lower magnitude than 'Y', which is a stimulus having a lower magnitude than 'Z'. Where 'X'', 'Y'' and 'Z'' are used below to quantify stimuli, 'X'' is a stimulus having a lower magnitude than 'Y'', which is a stimulus having a lower magnitude than 'Z'', where 'X'', 'Y'' and 'Z'' are opposite polarity to X', 'Y' and 'Z'.

Example 1

If the signal received by the chips (103, 108) indicates that the greatest degree of separation between the two contact lenses exists (i.e. the user is 'distance viewing') which is obviously greater than the degree of separation when the lenses are in their relaxed states, the chips (103, 108) produce a signal of a given polarity proportional to the difference between the respective degrees of separation.

If the signal received by the chips (103, 108) indicates that the degree of separation has slightly reduced, for example, which is indicative of 'moderate distance viewing', the chips (103, 108) produce a signal of lesser magnitude, proportional to the difference between the respective degrees of separation.

For example, where the lenses are in their relaxed state, the signal strength will be zero. When the lenses are being used for 'moderate distance viewing', e.g. where they have a degree of separation of 64 mm, the signal strength will be X. Where the lenses are being used for 'distance viewing', e.g. where they have a degree of separation of 65 mm, the signal strength will be Y.

If the signal received by the chips (103, 108) indicates that the degree of separation between the contact lenses is less than that when the lenses are in their relaxed states, the chips (103, 108) emit a signal of opposite polarity proportional to the difference. If the lowest degree of separation exists

| FIG. | Lens (Right, Left) | Intelligent Polymer Insert (Right, Left) | Power Cell (Right, Left) | Chip Emitting Signal (Right) | Chip Receiving Signal (Right, Left) | Chip Controlling Emission of Stimulus (Right, Left) | Wire (Right, Left) | Stabilising Feature (Right, Left) |
|---|---|---|---|---|---|---|---|---|
| 8 | 701, 706 | N/A | 702, 707 | 703 | 703, 708 | 703, 708 | 704, 709 | 705, 710 |
| 9 | 801, 807 | N/A | 802, 808 | 803 | 804, 809 | 804, 809 | 805, 810 | 806, 811 |
| 10 | 901, 905 | N/A | 902, 906 | 902 | 902, 906 | 902, 906 | 903, 907 | 904, 908 |
| 11 | 1001, 1007 | 1002, 1008 | 1003, 1009 | 1004 | 1004, 1010 | 1004, 1010 | 1005, 1011 | 1006, 1012 |
| 12 | 1101, 1108 | 1102, 1109 | 1103, 1110 | 1104 | 1105, 1111 | 1105, 1111 | 1106, 1112 | 1107, 1113 |
| 13 | 1201, 1206 | 1202, 1209 | 1203, 1207 | 1203 | 1203, 1207 | 1203, 1207 | 1204, 1208 | 1205, 1210 | between the lenses (i.e. the user is 'near viewing), then the chips (103, 108) produce a signal of opposite polarity proportional to the difference between the respective degrees of separation.

If the signal received by the chips (103, 108) indicates that the degree of separation has slightly increased, for example, which is indicative of 'moderate near viewing', the chips (103, 108) produce a signal of lesser magnitude, proportional to the difference between the respective degrees of separation.

For example, where the lenses are in their relaxed state, the signal strength will be zero. When the lenses are being used for 'moderate near viewing', e.g. where they have a degree of separation of 62 mm, the signal strength will be X'. Where the lenses are being used for 'near viewing', e.g. where they have a degree of separation of 61 mm, the signal strength will be Y'.

Example 2

If the signal received by the chips (103, 108) indicates that the degree of separation between the two contact lenses is greater than the degree of separation when the lenses are in their relaxed states, the chips (103, 108) produce a signal of a single amplitude and of a fixed polarity.

For example, where the lenses are in their relaxed state, the signal strength will be zero. When the lenses are being used for 'moderate distance viewing', e.g. where they have a degree of separation of 64 mm, the signal strength will be X. Where the lenses are being used for 'distance viewing', e.g. where they have a degree of separation of 65 mm, the signal strength will be X.

If the signal received by the chips (103, 108) indicates that the degree of separation between the contact lenses is less than that when the lenses are in their relaxed states, the chips (103, 108) emit a signal of opposite polarity proportional to the difference. If the lowest degree of separation exists between the lenses (i.e. the user is 'near viewing), then the chips (103, 108) produce a signal of opposite polarity proportional to the difference between the respective degrees of separation.

If the signal received by the chips (103, 108) indicates that the degree of separation has slightly increased, for example, which is indicative of 'moderate near viewing', the chips (103, 108) produce a signal of lesser magnitude, proportional to the difference between the respective degrees of separation.

For example, where the lenses are in their relaxed state, the signal strength will be zero. When the lenses are being used for 'moderate near viewing', e.g. where they have a degree of separation of 62 mm, the signal strength will be X'(an arbitrary unit). Where the lenses are being used for 'near viewing', e.g. where they have a degree of separation of 61 mm, the signal strength will be Y'.

Example 3

If the signal received by the chips (103, 108) indicates that the lowest degree of separation between the two contact lenses exists (i.e. the user is 'near viewing') which is obviously lesser than the degree of separation when the lenses are in their relaxed states, the chips (103, 108) produce a signal of a given polarity proportional to the difference between the respective degrees of separation.

If the signal received by the chips (103, 108) indicates that the degree of separation has slightly increased, for example, which is indicative of 'moderate near viewing', the chips (103, 108) produce a signal of lesser magnitude, proportional to the difference between the respective degrees of separation.

For example, where the lenses are in their relaxed state, the signal strength will be zero. When the lenses are being used for 'moderate near viewing', e.g. where they have a degree of separation of 62 mm, the signal strength will be X (an arbitrary unit). Where the lenses are being used for 'near viewing', e.g. where they have a degree of separation of 61 mm, the signal strength will be Y.

If the signal received by the chips (103, 108) indicates that the degree of separation between the contact lenses is greater than that when the lenses are in their relaxed states, the chips (103, 108) emit a signal of opposite polarity proportional to the difference. If the greatest degree of separation exists between the lenses (i.e. the user is 'distance viewing), then the chips (103, 108) produce a signal of opposite polarity proportional to the difference between the respective degrees of separation.

If the signal received by the chips (103, 108) indicates that the degree of separation has slightly decreased, for example, which is indicative of 'moderate distance viewing', the chips (103, 108) produce a signal of lesser magnitude, proportional to the difference between the respective degrees of separation.

For example, where the lenses are in their relaxed state, the signal strength will be zero. When the lenses are being used for 'moderate distance viewing', e.g. where they have a degree of separation of 64 mm, the signal strength will be X'. Where the lenses are being used for 'distance viewing', e.g. where they have a degree of separation of 65 mm, the signal strength will be Y'.

Example 4

If the signal received by the chips (103, 108) indicates that the degree of separation between the two contact lenses is lesser than the degree of separation when the lenses are in their relaxed states, the chips (103, 108) produce a signal of a single amplitude and of a fixed polarity.

For example, where the lenses are in their relaxed state, the signal strength will be zero. When the lenses are being used for 'moderate near viewing', e.g. where they have a degree of separation of 62 mm, the signal strength will be X. Where the lenses are being used for 'near viewing', e.g. where they have a degree of separation of 61 mm, the signal strength will be X. If the signal received by the chips (103, 108) indicates that the degree of separation between the contact lenses is greater than that when the lenses are in their relaxed states, the chips (103, 108) emit a signal of opposite polarity proportional to the difference. If the greatest degree of separation exists between the lenses (i.e. the user is 'distance viewing), then the chips (103, 108) produce a signal of opposite polarity proportional to the difference between the respective degrees of separation.

If the signal received by the chips (103, 108) indicates that the degree of separation has slightly decreased, for example, which is indicative of 'moderate distance viewing', the chips (103, 108) produce a signal of lesser magnitude, proportional to the difference between the respective degrees of separation.

For example, where the lenses are in their relaxed state, the signal strength will be zero. When the lenses are being used for 'moderate distance viewing', e.g. where they have a degree of separation of 64 mm, the signal strength will be X'(an arbitrary unit). Where the lenses are being used for 'distance viewing', e.g. where they have a degree of separation of 65 mm, the signal strength will be Y'.

Example 5

If the signal received by the chips (103, 108) indicates that the degree of separation between the two contact lenses exceeds a 'distance threshold', the chips (103, 108) produce a signal of a single amplitude and of a fixed polarity.

The lenses may be arranged such that the 'distance threshold' is any distance ranging from the degree of separation when the lenses are in the relaxed state and when the degree of separation is at its greatest. In certain embodiments, the distance threshold will be met where the degree of separation is greater than that at which the lenses are in the relaxed state.

For example, where the lenses are in their relaxed state (e.g. at a degree of separation of 63.0 mm), the signal strength will be zero. When the degree of separation increases above 63.0 mm, and the distance threshold is exceeded (>63.0 mm), a fixed stimulus of, for example, X will be emitted.

If the signal received by the chips (103, 108) indicates that the degree of separation between the two contact lenses passes a 'near vision threshold', the chips (103, 108) produce a signal of a single amplitude and of a fixed polarity.

The lenses may be arranged such that the 'near vision threshold' is any distance between the degree of separation when the lenses are in the relaxed state and when the degree of separation is at its lowest. In certain embodiments, the near vision threshold will be met where the degree of separation is lower than that at which the lenses are in the relaxed state.

For example, where the lenses are in their relaxed state (e.g. at a degree of separation of 63.0 mm), the signal strength will be zero. When the degree of separation reduces below 63.0 mm, and the near vision threshold is passed (<63.0 mm), a fixed stimulus of, for example, X' will be emitted.

Example 6

If the signal received by the chips (103, 108) indicates that the lowest angle of convergence exists between the two contact lenses (i.e. the user is 'distance viewing') which will obviously be lower than the angle of convergence when the lenses are in their relaxed states, the chips (103, 108) produce a signal of a given polarity proportional to the difference between the respective angles of convergence.

If the signal received by the chips (103, 108) indicates that the angle of convergence has slightly increased, for example, which is indicative of 'moderate distance viewing', the chips (103, 108) produce a signal of lesser magnitude, proportional to the difference between the respective angles of convergence.

For example, where the lenses are in their relaxed state, the signal strength will be zero. When the lenses are being used for 'moderate distance viewing', e.g. where they have a convergence angle of 2° the signal strength will be X. Where the lenses are being used for 'distance viewing', e.g. where they have an angle of convergence of separation of 0°, the signal strength will be Y.

If the signal received by the chips (103, 108) indicates that the angle of convergence between the contact lenses is greater than that when the lenses are in their relaxed states, the chips (103, 108) emit a signal of opposite polarity proportional to the difference. If the greatest angle of convergence exists between the lenses (i.e. the user is 'near viewing), then the chips (103, 108) produce a signal of opposite polarity proportional to the difference between the respective angles of convergence.

If the signal received by the chips (103, 108) indicates that the convergence angle has slightly decreased, for example, which is indicative of 'moderate near viewing', the chips (103, 108) produce a signal of lesser magnitude, proportional to the difference between the respective angles of convergence.

For example, where the lenses are in their relaxed state, the signal strength will be zero. When the lenses are being used for 'moderate near viewing', e.g. where they have an angle of convergence of 6°, the signal strength will be X'. Where the lenses are being used for 'near viewing', e.g. where they have a convergence angle of 8°, the signal strength will be Y'.

Example 7

If the signal received by the chips (103, 108) indicates that the angle of convergence between the two contact lenses is lower than the degree of separation when the lenses are in their relaxed states, the chips (103, 108) produce a signal of a single amplitude and of a fixed polarity.

For example, where the lenses are in their relaxed state, the signal strength will be zero. When the lenses are being used for 'moderate distance viewing', e.g. where they have a convergence angle of 3.7°, the signal strength will be X (an arbitrary unit). Where the lenses are being used for 'distance viewing', e.g. where they have an angle of convergence of 0°, the signal strength will be X.

If the signal received by the chips (103, 108) indicates that the angle of convergence between the contact lenses is greater than that when the lenses are in their relaxed states, the chips (103, 108) emit a signal of opposite polarity proportional to the difference. If the greatest angle of convergence exists between the lenses (i.e. the user is 'near viewing), then the chips (103, 108) produce a signal of opposite polarity proportional to the difference between the respective angles of convergence.

If the signal received by the chips (103, 108) indicates that the convergence angle has slightly decreased, for example, which is indicative of 'moderate near viewing', the chips (103, 108) produce a signal of lesser magnitude, proportional to the difference between the respective angles of convergence.

For example, where the lenses are in their relaxed state, the signal strength will be zero. When the lenses are being used for 'moderate near viewing', e.g. where they have an angle of convergence of 5.7°, the signal strength will be X'(an arbitrary unit). Where the lenses are being used for 'near viewing', e.g. where they have a convergence angle of 9.2°, the signal strength will be Y'.

Example 8

If the signal received by the chips (103, 108) indicates that the greatest angle of convergence between the contact lenses exists (i.e. the user is 'near viewing') which is greater than the angle between the lenses when in their relaxed states, the chips (103, 108) produce a signal of a given polarity proportional to the difference between the respective angles of convergence.

If the signal received by the chips (103, 108) indicates that the convergence angle has slightly decreased, for example, which is indicative of 'moderate near viewing', the chips (103, 108) produce a signal of lesser magnitude, proportional to the difference between the respective angles of convergence.

For example, where the lenses are in their relaxed state, the signal strength will be zero. When the lenses are being used for 'moderate near viewing', e.g. where they have an angle of convergence of 5.7°, the signal strength will be X (an arbitrary unit). Where the lenses are being used for 'near viewing', e.g. where they have a convergence angle of 9.2°, the signal strength will be Y.

If the signal received by the chips (103, 108) indicates that the angle between the contact lenses is smaller than that when the lenses are in their relaxed states, the chips (103, 108) emit a signal of opposite polarity proportional to the difference. If the smallest angle exists between the lenses (i.e. the user is 'distance viewing'), then the chips (103, 108) produce a signal of opposite polarity proportional to the difference between the respective angles between the contact lenses.

If the signal received by the chips (103, 108) indicates that the angle between the contact lenses has slightly increased, for example, which is indicative of 'moderate distance viewing', the chips (103, 108) produce a signal of lesser magnitude, proportional to the difference between the respective angles.

For example, where the lenses are in their relaxed state, the signal strength will be zero. When the lenses are being used for 'moderate distance viewing', e.g. where they have an angle between the lenses of 3.7° the signal strength will be X'. Where the lenses are being used for 'distance viewing', e.g. an angle between the lenses of 0°, the signal strength will be Y'.

Example 9

If the signal received by the chips (103, 108) indicates that the convergence angle between the two contact lenses is greater than the angle of convergence when the lenses are in their relaxed states, the chips (103, 108) produce a signal of a single amplitude and of a fixed polarity.

For example, where the lenses are in their relaxed state, the signal strength will be zero. When the lenses are being used for 'moderate near viewing', e.g. where they have an angle of convergence of 6.2°, the signal strength will be X. Where the lenses are being used for 'near viewing', e.g. where they have a convergence angle of 9.2°, the signal strength will be X.

If the signal received by the chips (103, 108) indicates that the angle of convergence between the contact lenses is lesser than that when the lenses are in their relaxed states, the chips (103, 108) emit a signal of opposite polarity proportional to the difference. If the lowest angle of convergence exists between the lenses (i.e. the user is 'distance viewing'), then the chips (103, 108) produce a signal of opposite polarity proportional to the difference between the respective angles of convergence.

If the signal received by the chips (103, 108) indicates that the convergence angle has slightly increased, for example, which is indicative of 'moderate distance viewing', the chips (103, 108) produce a signal of lesser magnitude, proportional to the difference between the respective angles of convergence.

For example, where the lenses are in their relaxed state, the signal strength will be zero. When the lenses are being used for 'moderate distance viewing', e.g. where they have a convergence angle of 4.6°, the signal strength will be X' (an arbitrary unit). Where the lenses are being used for 'distance viewing', e.g. where they have an angle of convergence of 0°, the signal strength will be Y'.

Example 10

If the signal received by the chips (103, 108) indicates that the angle of convergence between the two contact lenses has passed a 'distance threshold', the chips (103, 108) produce a signal of a single amplitude and of a fixed polarity.

The lenses may be arranged such that the 'distance threshold' is any convergence angle ranging from the convergence angle when the lenses are in the relaxed state and when the angle of convergence is at its lowest. In certain embodiments, the distance threshold will be met where the angle of convergence is lesser than that at which the lenses are in the relaxed state.

For example, where the lenses are in their relaxed state (e.g. at a convergence angle of 5.6°), the signal strength will be zero. When the convergence angle is reduced below 5.6°, and the distance threshold is exceeded)(<5.6°, a fixed stimulus of, for example, X will be emitted.

If the signal received by the chips (103, 108) indicates that the angle of convergence between the two contact lenses exceeds a 'near vision threshold', the chips (103, 108) produce a signal of a single amplitude and a fixed polarity.

The lenses may be arranged such that the 'near vision threshold' is any angle between the convergence angle when the lenses are in the relaxed state and when the convergence angle is at its greatest. In certain embodiments, the near vision threshold will be met where the angle of convergence is greater than that at which the lenses are in the relaxed state.

For example, where the lenses are in their relaxed state (e.g. at a convergence angle of 5.6°), the signal strength will be zero. When the convergence angle is increased above 5.6°, and the near vision threshold is passed)(>5.6°, a fixed stimulus of, for example, X' will be emitted.

The invention claimed is:

1. A contact lens that comprises an intelligent polymer, the contact lens having a relaxed state which, upon application of a first stimulus, forms a first corrective shape and which, upon application of a second stimulus, forms a second corrective shape, wherein a corrective effect provided by the contact lens in the relaxed state is intermediate to corrective visual effects provided by the first corrective shape and the second corrective shape, and the contact lens reverts to the relaxed state following cessation of the first stimulus or the second stimulus.

2. The contact lens of claim 1, wherein the corrective visual effect provided by the first corrective shape is a near addition correction.

3. The contact lens of claim 1, wherein the corrective visual effect provided by the second corrective shape is a distance correction.

4. The contact lens of claim 1, wherein the first corrective shape and the second corrective shape differ in terms of the degree of curvature of the contact lens.

5. The contact lens of claim 1, wherein the change in lens shape upon the application of the first stimulus and/or the second stimulus is localised to a front surface and/or a back surface and/or an embedded zone within the contact lens.

6. The contact lens of claim 5, wherein the embedded zone is located within a gas filled cavity within the contact lens.

7. The contact lens of claim 5, wherein the embedded zone comprises a gas-filled cavity which is either partially or totally surrounded by the intelligent polymer.

8. The contact lens of claim 1, wherein a back surface and/or a front surface of the contact lens are toric and/or aspheric.

9. The contact lens of claim 1, wherein the contact lens is an intraocular lens.

10. The contact lens of claim 1, wherein the contact lens is a corneal inlay or onlay lens.

11. The contact lens of claim 1, wherein the first stimulus has a positive polarity and the second stimulus has a negative polarity.

12. The contact lens of claim 1, wherein the first stimulus and the second stimulus are electric fields.

13. The contact lens of claim 1, wherein the first stimulus or the second stimulus is produced by a stimulus emission emitter.

14. The contact lens of claim 13, wherein the stimulus emission emitter comprises a chip embedded within the contact lens.

15. The contact lens of claim 13, wherein the stimulus emission emitter comprises a nano chip, a micro chip, an environmental energy harvesting cell, a body energy harvesting cell, or any combination thereof.

16. The contact lens of claim 1, further comprising a chip for monitoring eye movement.

17. The contact lens of claim 16, wherein the chip is embedded in the contact lens.

18. The contact lens of claim 16, wherein the chip is a nano chip or micro chip.

19. The contact lens of claim 18, wherein the chip monitors a distance between right and left contact lenses and emits the first stimulus or the second stimulus when the distance changes.

20. The contact lens of claim 18, wherein the chip is capable of emitting the first stimulus and/or the second stimulus at a range of magnitudes.

21. The contact lens of claim 16, wherein the chip monitors the eye movement such that a change in the eye movement causes the chip to emit the first stimulus or the second stimulus or to alter the magnitude of the first stimulus or the second stimulus, if already emitted.

22. The contact lens of claim 16, wherein the chip monitors lines of sight such that a change in an angle of convergence causes the chip to emit the first stimulus or the second stimulus or to alter the magnitude of the first stimulus or the second stimulus, if already emitted.

23. The contact lens of claim 16, wherein the chip tracks rotation of the contact lens such that a change in the rotation causes the chip to emit the first stimulus or the second stimulus or to alter the magnitude of the first stimulus or the second stimulus, if already emitted.

24. The contact lens of claim 16, wherein the chip monitors an inter-pupillary distance from the centre of a user's pupil and emits the first stimulus or the second stimulus when the inter-pupillary distance changes.

25. The contact lens of claim 1, wherein the contact lens comprises a single region of the intelligent polymer.

26. The contact lens of claim 1, wherein the contact lens comprises a plurality of regions of the intelligent polymer.

27. The contact lens of claim 26, wherein each of the plurality of regions of the intelligent polymer produces the same type of effect upon the emission of the first stimulus and the second stimulus.

28. The contact lens of claim 1, wherein the contact lens is formed substantially or completely of the intelligent polymer.

29. The contact lens of claim 1, wherein the contact lens comprises hydrogels, silicone hydrogels, silicone polymers, poly(urethanes), poly(siloxanes), silicones, poly(methyl methacrylate), poly(vinyl alcohol), poly(ethylenes), poly (vinyl pyrrolidone), poly(methacrylic acid), poly(acrylamide), poly(ethylene oxide), poly(acrylic) acid, poly(propylene oxide), poly(2-hydroxy ethyl methacrylate), or mixtures thereof.

30. The contact lens of claim 1, wherein the intelligent polymer comprises at least one electronic electrically activated polymer and/or at least one ionic electrically activated polymer.

31. The contact lens of claim 30, wherein the electronic electrically activated polymer comprises dielectric EAPs, electrostrictive elastomers, electro-viscoelastic elastomers, piezoelectric polymers, ferroelectric polymers, poly[(vinylidenefluoride-co-trifluoroethylene] [P(VDF-TrFE)]), carbon nanotube aerogel, or mixtures thereof.

32. The contact lens of claim 30, where the ionic electrically activated polymer comprises polymer gels, polyelectrolyte materials, ionic polymers (optionally including metal composites), ion-exchange polymer metal matrix composites (IPMC), electro conducting conjugated polymer, carbon nanotubes, or mixtures thereof.

33. The contact lens of claim 1, wherein the intelligent polymer comprises chitosan, chondroitin sulfate, hyaluronic acid, alginate, vinyl alcohol, allylamine, acrylonitrile, 2-acrylamido-2-methypropane sulfonic acid, aniline, 2-hydroxyethyl methacrylate, methacrylic acid, acrylic acid, vinyl sulfonic acid, poly(2-hydroxyethyl methacrylate), chitosan, poly(vinyl alcohol), poly(sodium maleate-co-sodium acrylate), alginate/poly(diallyldimethylamomium chloride), acrylic acid/vinyl sulfonic acid hydrogel, hydrogel based on polyacrylic acid/polyvinyl sulfonic acid, poly(acrylic acid)-co-(acrylamide) gels, acrylic acid acrylamide copolymere gels PAAm, poly(vinyl alcohol)-poly(acrylic acid) gels, poly(vinyl alcohol)-poly(sodium acrylate), polyacrylic acid with sodium acrylate crosslinked with bisacrylamide, polyacrylonitrile, polysodium acrylate (PAANa), Gelatin/poly (hydroxyethylmethacrylate) hydrogel, vinyl polymer poly (dimethyl siloxane) with $TiO_2$ particles, or mixtures thereof.

34. The contact lens of claim 1, wherein the intelligent polymer comprises magnetite, ferrogels, metallic particles, metallic plating, metal composite particles, metal composite plating, semiconducting polymer particles, polyN-isopropylacrylamide poly(hydroxyethyl methacrylate), styrene-ethylene/butylene-styrene triblock polymer gels, ethylene vinyl alcohol, additives, or mixtures thereof.

35. The contact lens of claim 1, further comprising a power source.

36. The contact lens of claim 35, wherein the power source is embedded within the contact lens.

37. The contact lens of claim 35, wherein the power source comprises an environmental energy harvesting cell, a body energy harvesting cell, a chemical cell, a pre-charged cell, or any combination thereof.

38. A pair of contact lenses, wherein one or both of the contact lenses is the contact lens of claim 1.

* * * * *